(12) United States Patent
Bennett et al.

(10) Patent No.: US 10,441,663 B2
(45) Date of Patent: Oct. 15, 2019

(54) METHODS FOR TREATING CANCER

(71) Applicant: Bicycle Therapeutics Limited, Cambridge (GB)

(72) Inventors: Gavin Bennett, Cambridge (GB); Daniel Paul Teufel, Cambridge (GB)

(73) Assignee: BICYCLERD LIMITED, Cambridge (GB)

( * ) Notice: Subject to any disclaimer, the term of this patent is extended or adjusted under 35 U.S.C. 154(b) by 0 days.

(21) Appl. No.: 15/822,437

(22) Filed: Nov. 27, 2017

(65) Prior Publication Data

US 2018/0169254 A1 Jun. 21, 2018

Related U.S. Application Data

(60) Provisional application No. 62/426,540, filed on Nov. 27, 2016, provisional application No. 62/443,422, filed on Jan. 6, 2017, provisional application No. 62/476,211, filed on Mar. 24, 2017, provisional application No. 62/562,795, filed on Sep. 25, 2017.

(51) Int. Cl.

| | | |
|---|---|---|
| *A61K 47/64* | (2017.01) | |
| *A61P 35/00* | (2006.01) | |
| *C07K 7/08* | (2006.01) | |
| *A61K 38/12* | (2006.01) | |
| *C07K 14/00* | (2006.01) | |

(52) U.S. Cl.
CPC .............. *A61K 47/64* (2017.08); *A61K 38/12* (2013.01); *A61P 35/00* (2018.01); *C07K 7/08* (2013.01); *C07K 14/00* (2013.01)

(58) Field of Classification Search
None
See application file for complete search history.

(56) References Cited

U.S. PATENT DOCUMENTS

| 9,994,617 B2 | 6/2018 | Tite et al. |
|---|---|---|
| 2014/0256596 A1 | 9/2014 | Tite et al. |

FOREIGN PATENT DOCUMENTS

| CN | 101497878 | | 8/2009 |
|---|---|---|---|
| WO | 2004077062 | | 9/2004 |
| WO | 2006078161 | | 7/2006 |
| WO | 2009098450 | | 8/2009 |
| WO | 2010089117 | | 8/2010 |
| WO | 2013050615 | | 4/2013 |
| WO | 2013050616 | | 4/2013 |
| WO | WO 2013050616 | * | 4/2013 |
| WO | 2016067035 | | 5/2016 |
| WO | WO 2016067035 | * | 5/2016 |
| WO | WO 2017/191460 | * | 9/2017 |
| WO | 2017191460 A1 | | 11/2017 |

OTHER PUBLICATIONS

Berge et al., "Pharmaceutical Salts," Journal of Pharmaceutical Sciences, vol. 66, No. 1, Jan. 1977 (pp. 1-19).
Chang et al., "Subtiligase: a tool for semisynthesis of proteins," Proceedings of the National Academy of Sciences, U.S.A., vol. 91, No. 26, Dec. 1994 (pp. 12544-12548).
Chen et al., "Cell-penetrating peptides in drug development: enabling intracellular targets," Biochemical Society Transactions, vol. 35, No. 4, Aug. 2007 (pp. 821-825).
Cherney et al., "Macrocyclic Amino Carboxylates as Selective MMP-8 Inhibitors," Journal of Medicinal Chemistry, vol. 41, No. 11, May 1998 (pp. 1749-1751).
Dawson et al., "Synthesis of proteins by native chemical ligation," Science, vol. 266, No. 5186, Nov. 1994 (pp. 776-779).
Derossi et al., "The third helix of the Antennapedia homeodomain translocates through biological membranes," Journal of Biological Chemistry, vol. 269, No. 14, Apr. 1994 (pp. 10444-10450).
Driggers et al., "The exploration of macrocycles for drug discovery—an underexploited structural class," Nature Reviews Drug Discovery, vol. 7, No. 7, Jul. 2008 (pp. 608-624).
Elson-Schwab et al., "Guanidinylated Neomycin Delivers Large, Bioactive Cargo into Cells through a Heparan Sulfate-dependent Pathway," Journal of Biological Chemistry, vol. 282, No. 18, May 2007 (pp. 13585-13591).
Gentilucci et al., "Chemical Modifications Designed to Improve Peptide Stability: Incorporation of Non-Natural Amino Acids, Pseudo-Peptide Bonds, and Cyclization," Current Pharmaceutical Design, vol. 16, No. 28, No Month Listed 2010 (pp. 3185-3203).
Gupta et al., "Intracellular delivery of large molecules and small particles by cell-penetrating proteins and peptides," Advanced Drug Delivery Reviews, vol. 57, No. 4, Feb. 2005 (pp. 637-651).
Heinis et al., "Phage-encoded combinatorial chemical libraries based on bicyclic peptides," Nature Chemical Biology, vol. 5, No. 7, Jul. 2009 (pp. 502-507).
Kellogg et al., "Disulfide-Linked Antibody-Maytansinoid Conjugates: Optimization of In Vivo Activity by Varying the Steric Hindrance at Carbon Atoms Adjacent to the Disulfide Linkage," Bioconjugate Chemistry, vol. 22, No. 4, Mar. 2011 (pp. 717-727).
Kemp et al., "Conformationally restricted cyclic nonapeptides derived from L-cysteine and LL-3-amino-2-piperidone-6-carboxylic acid (LL-Acp), a potent .beta.-turn-inducing dipeptide analog," The Journal of Organic Chemistry, vol. 50, No. 26, Dec. 1985 (pp. 5834-5838).
Nestor, "The medicinal chemistry of peptides," Current Medicinal Chemistry, vol. 16, No. 33, No Month Listed 2009 (pp. 4399-4418).
Oehlke et al., "Cellular uptake of an alpha-helical amphipathic model peptide with the potential to deliver polar compounds into the cell interior non-endocytically," Biochimica et Biophysica Acta, vol. 1414, No. 1-2, Nov. 1998 (pp. 127-139).
Okuyama et al., "Small-molecule mimics of an a-helix for efficient transport of proteins into cells," Nature Methods, vol. 4, No. 2, Feb. 2007 (pp. 153-159).
Purdie et al., "Piperazinedione formation from esters of dipeptides containing glycine, alanine, and sarcosine: the kinetics in aqueous solution," Journal of the Chemical Society, Perkin Transactions 2, vol. 0, No. 14, No Month Listed 1973 (pp. 1845-1852).
Qi et al., "Serial determination of glomerular filtration rate in conscious mice using FITC-inulin clearance," American Journal of Physiology—Renal Physiology, vol. 286, No. 3, Mar. 2004 (pp. F590-F596).
Remacle et al., "Novel MT1-MMP small-molecule inhibitors based on insights into hemopexin domain function in tumor growth," Cancer Research, vol. 72, No. 9, May 2012 (pp. 2339-2349).

(Continued)

*Primary Examiner* — Maury A Audet
(74) *Attorney, Agent, or Firm* — Andrea L. C. Reid; Dechert LLP

(57) ABSTRACT

The present invention relates to a method of treating cancer in a subject.

22 Claims, 8 Drawing Sheets

(56) References Cited

OTHER PUBLICATIONS

Schreiber et al., "Rapid, electrostatically assisted association of proteins," Nature Structural & Molecular Biology, vol. 3, May 1996 (pp. 427-431).

Sounni et al., "MT1-MMP expression promotes tumor growth and angiogenesis through an up-regulation of vascular endothelial growth factor expression," The FASEB Journal, vol. 16, No. 6, Apr. 2002 (pp. 555-564).

Suojanen et al., "A novel and selective membrane type-1 matrix metalloproteinase (MT1-MMP) inhibitor reduces cancer cell motility and tumor growth," Cancer Biology & Therapy, vol. 8, No. 24, Dec. 2009 (pp. 2362-2370).

Timmerman et al., "Rapid and quantitative cyclization of multiple peptide loops onto synthetic scaffolds for structural mimicry of protein surfaces," Chembiochem, vol. 6, No. 5, May 2005 (pp. 821-824).

Tugyi et al., "Partial D-amino acid substitution: Improved enzymatic stability and preserved Ab recognition of a MUC2 epitope peptide," Proceedings of the National Academy of Sciences U.S.A., vol. 102, No. 2, Jan. 2005 (pp. 413-418).

Wang, "An exact mathematical expression for describing competitive binding of two different ligands to a protein molecule," FEBS Letters, vol. 360, No. 2, Feb. 1995 (pp. 111-114).

Wu et al., "Structures of the CXCR4 chemokine GPCR with small-molecule and cyclic peptide antagonists," Science, vol. 330, No. 6007, Nov. 2010 (pp. 1066-1071).

Xiong et al., "Crystal structure of the extracellular segment of integrin alpha Vbeta3 in complex with an Arg-Gly-Asp ligand," Science, vol. 296, No. 5565, Apr. 2002 (pp. 151-155).

Yoshihara et al., "Tags for labeling protein N-termini with subtiligase for proteomics," Bioorganic & Medicinal Chemistry Letters, vol. 18, No. 22, Nov. 2008 (pp. 6000-6003).

Zarrabi et al., "Inhibition of matrix metalloproteinase 14 (MMP-14)-mediated cancer cell migration," Journal of Biological Chemistry, vol. 286, No. 38, Sep. 2011 (pp. 33167-33177).

Zhao et al., "Structural basis of specificity of a peptidyl urokinase inhibitor, upain-1," Journal of Structural Biology, vol. 160, No. 1, Oct. 2007 (10 pages).

Bennett et al., "Development of BT1718, a Bicycle Drug Conjugate® (BDC) targeting MT1-MMP for treatment of solid tumours," European Journal of Cancer, vol. 69, Supplement 1, Nov. 2016 (p. S21).

Harrison et al., "Abstract 5144: BT1718, a novel bicyclic peptide-maytansinoid conjugate targeting MT1-MMP for the treatment of solid tumors: Design of bicyclic peptide and linker selection," Cancer Research, vol. 77, No. 13, Supplement, Jul. 2017 (1 page).

International Search Report and Written Opinion issued by the European Patent Office as Searching Authority for International Application No. PCT/GB2017/053560 dated Feb. 7, 2018 (9 pages).

U.S. Appl. No. 15/523,266 of Teufel et al., filed Apr. 28, 2017.

* cited by examiner

METHODS FOR TREATING CANCER

BACKGROUND OF THE INVENTION

MT1-MMP is a transmembrane metalloprotease that plays a major role in the extracellular matrix remodelling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumors. Accordingly, there remains a high unmet need in developing inhibitors of MT1-MMP for the treatment of cancer

DETAILED DESCRIPTION OF CERTAIN EMBODIMENTS OF THE INVENTION

1. Compound

Figure 1:
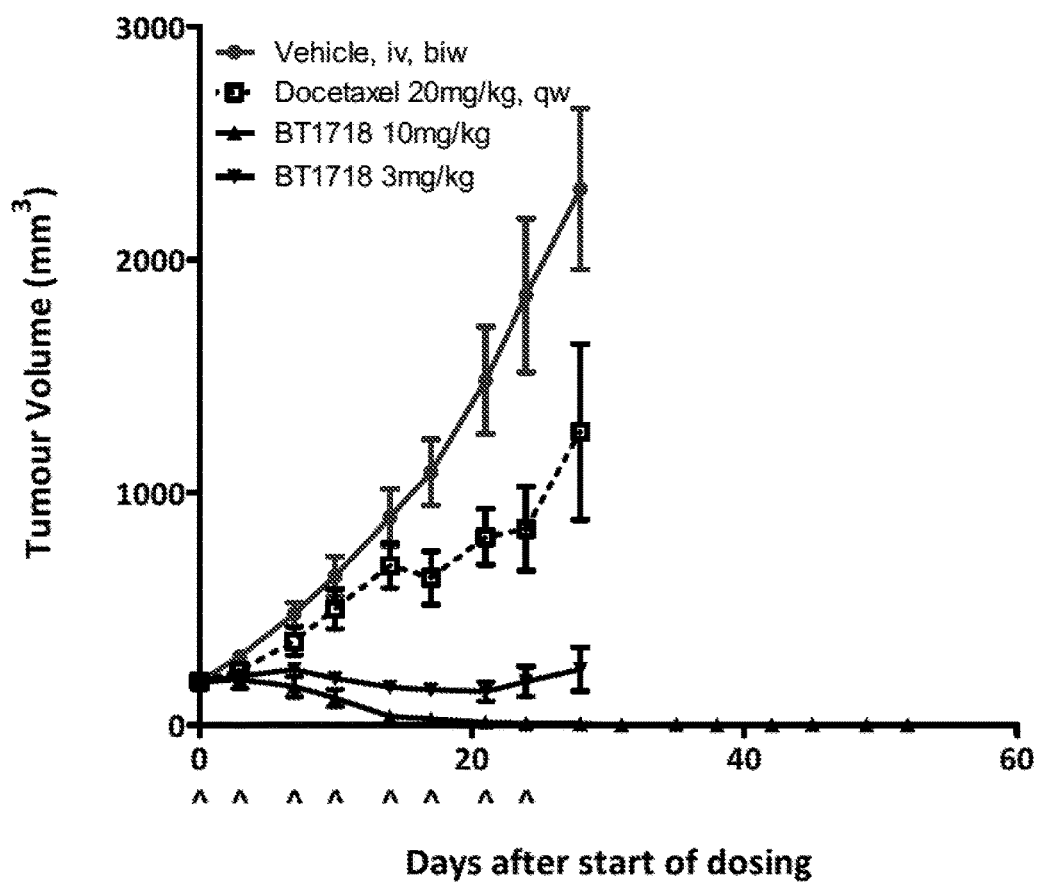
FIG. 1 depicts the efficacy of BT1718 in the LU-01-0046 non-small-cell lung carcinoma (NSCLC) patient-derived xenograft (PDX) animal model.

A proprietary phage display and cyclic peptide technology (Bicycle technology) was utilized to identify high affinity binding peptides to the membrane type 1-matrix metalloproteinase (MT1-MMP/MMP14). MT1-MMP (MT1) is a cell surface membrane protease normally involved in tissue remodeling which has been found to be over-expressed in many solid tumors. Overexpression of MT1 has been linked to cancer invasiveness and poor prognosis. While attempts to target the proteolytic activity of MT1 and other MMPs in cancer were unsuccessful in clinical trials largely due to toxicity caused by insufficient selectivity, MT1-MMP remains an attractive cancer target for targeted cytotoxic delivery approaches.

Diverse selection phage libraries containing $10^{11}$ to $10^{13}$ unique peptide sequences which are post-translationally cyclized with thiol-reactive scaffolds were used to identify small (1.5-2 kDa) constrained bicyclic peptides binders (Bicycles) to the hemopexin domain of MT1. Initial binders were subject to affinity maturation by directed screens and stabilization by chemical optimization.

A bicyclic constrained peptide binder (Bicycle) was identified that binds to the hemopexin domain of MT1 with an apparent Kd of approximately 2 nM. The Bicycle peptide (N241) binds with similar affinity to the entire ectodomain of the protease but shows no binding to the catalytic domain. N241 also shows no binding toward any of the closely related MMP family members tested (MMP15, MMP16, MMP24, MMP1, Pro-MMP1, MMP2). Characterization of the pharmacologic effect of N241 on MT1 in vitro shows that the peptide has no direct impact on the catalytic activity of the protease, nor related MMP catalytic activity (MMP1, MMP2 and MMP9) nor cell migration or invasion. However, binding of fluorescently-tagged N241 to MT1 on HT1080 fibrosarcoma cells results in the rapid internalization and subsequent lysosomal localization of the compound. In addition, $^{177}$Lu-loaded N241 demonstrates rapid tumor localization when injected IV into mice bearing MT1-positive tumor xenografts, with levels as high as 15-20% injected dose per gram of tumor in less than 60 minutes. In contrast, a non-binding Bicycle peptide shows no tumor localization. These properties suggest that N241 may be a good delivery vehicle for cytotoxic payloads targeting MT1-positive tumor cells. Bicycle drug conjugates (BDCs) with a variety of linkers and cytotoxic payloads were prepared which retained binding to MT1. The anti-tumor activity of select BDCs was demonstrated in MT1-positive human tumor cell xenografts in mice.

BT1718 is a Bicycle drug conjugate (BDC) comprising a constrained bicyclic peptide that binds with high affinity and specificity to membrane type 1-matrix metalloprotease (MT1-MMP; MMP14) covalently linked through a hindered disulfide linker to the potent anti-tubulin agent DM1. MT1-MMP is naturally involved in tissue remodeling, however overexpression of the cell-surface protease has been tied to tumor aggressiveness and invasiveness, as well as poor patient prognosis for many cancer indications. The Bicycle binder for BT1718 (N241) was identified using a proprietary phage display peptide technology consisting of highly diverse phage libraries of linear amino acid sequences constrained into two loops by a central chemical scaffold. While binding with similar affinity and specificity to that observed with monoclonal antibodies, the small size of a Bicycle peptide (1.5-2 kDa) aids in its rapid extravasation and tumor penetration making it an ideal format for the targeted delivery of cytotoxic payloads.

A series of maytansinoid-BDC conjugates were prepared, with varying linker format to adjust cleavability and evaluated for their anti-tumor activity in an MT1-positive tumor xenograft model. The BDC selected for further assessment (BT1718) was evaluated for efficacy in an array of tumor xenograft models.

A mono-hindered linker-DM1 construct (BT1718) was among the most active constructs against MT1-positive EBC-1 lung tumor xenografts. Efficacy in this model was reduced in the conjugates containing the least cleavable linkers. Dosing BT1718 on a twice weekly schedule for two weeks, significant reduction in tumor growth was seen at 3 mg/kg, with 10 mg/kg causing complete regressions in this model. Effective treatment was also seen with same total dose, given at on schedules from daily to a single weekly dose. Treatment with BT1718 in a selection of MT1-positive tumor xenograft models (e.g. HT1080 fibrosarcoma; HCC1806 triple negative breast cancer; SNU-16 gastric cancer) demonstrated activity at minimally effective doses in the range of 3-10 mg/kg weekly or twice weekly, with 10 mg/kg twice weekly causing complete regressions in most models. Preliminary metabolism studies indicate that BT1718 is excreted mainly through the kidney in urine.

BT1718, a Bicycle drug conjugate (BDC), shows potent antitumor activity in human tumor xenograft models of fibrosarcoma, lung and breast cancer. Without wishing to be bound by any particular theory, it is believed that the small size of the BDC may offer a significant advantage to other targeted cytotoxic approaches such as antibody-drug conjugates due to rapid extravasation and improved tumor penetration.

In certain aspects, the present invention provides a method of treating certain cancers in a subject, comprising administering to the subject an effective amount of a drug conjugate comprising a high affinity binder of MT1-MMP, such as BT1718, or a pharmaceutically acceptable salt or composition thereof.

Preparation of BT1718 is described in detail in WO 2016/067035, filed Oct. 29, 2015, the entirety of which is hereby incorporated herein by reference. BT1718 has the structure shown below.

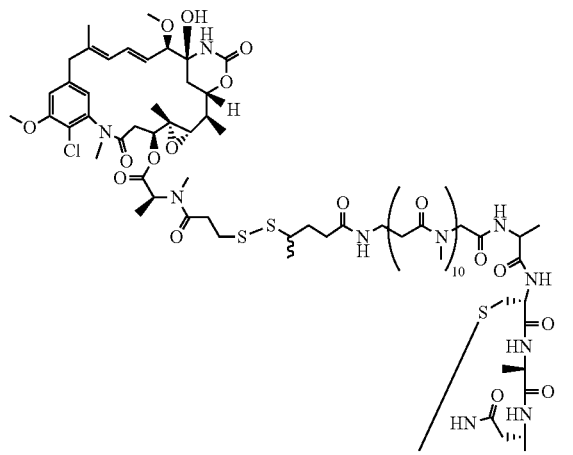

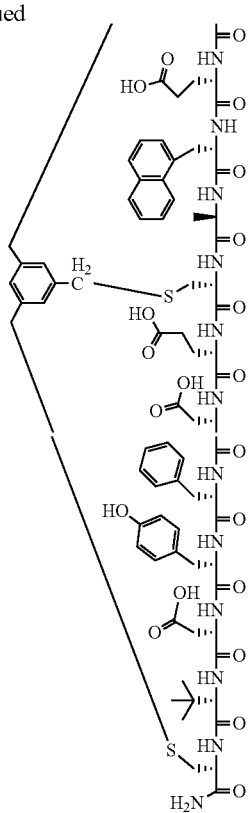

It was surprisingly found that BT1718 is highly active across the tumor types shown in Table 1. In some embodiments, the cancer is selected from a tumor type in Table 1, below. In some embodiments, the tumor cell type is one of those in Table 1, below. In some embodiments, the minimally effective dose is one of those shown in Table 1, below.

TABLE 1

| Tumor Indication | Model | Minimally Effective Dose* IV BIW | Best response at 10 mg/kg | Annotations |
|---|---|---|---|---|
| Sarcoma | HT1080 | <3 mg/kg | CR | Fibrosarcoma - N-ras mutant/ IDH1 mutant soft tissue sarcoma (STS) |
| Lung | EBC-1 | <10 mg/kg | CR | Met-amplified squamous NSCLC |
| | NCI-H292 | <10 mg/kg | CR | Squamous cell NSCLC with wt EGFR |
| | NCI-H1975 | <10 mg/kg | CR | T790M EGFR-expressing lung adenocarcinoma |
| Breast | MDA-MB-231 | <10 mg/kg | CR | Triple negative breast cancer |
| | HCC-1806 | <10 mg/kg | CR | Basaloid triple negative breast cancer |
| Colon | HCT-15 | >10 mg/kg | Growth delay | High pgp-expressing colorectal adenocarcinoma |
| | HT-29 | 10 mg/kg | PR | Colorectal adenocarcinoma |

TABLE 1-continued

| Tumor Indication | Model | Minimally Effective Dose* IV BIW | Best response at 10 mg/kg | Annotations |
|---|---|---|---|---|
| Gastric | SNU-16 | 3 mg/kg | CR | FGFR-amplified gastric cancer |
| Head & Neck | RPMI2650 | 10 mg/kg | PR | Nasal septum squamous cell carcinoma |

*MED - dose leading to tumor-stasis; CR complete response; PR partial response

As mentioned above, a mono-hindered linker-DM1 construct (BT1718) was among the most active constructs against MT1-positive EBC-1 lung tumor xenografts. By means of comparison, a non-reducible BDC was prepared, BT1721, which includes a non-reducible maleimide thioether linkage which is proteolytically labile. Although BT1718 and BT1723 have similar binding affinities to MT1-MMP as measured by fluorescence polarisation competition (BT1718 $K_i$=0.9 nM versus BT1721 $K_i$=1.1 nM; the fluorescence polarisation competition assay is described in detail in WO 2016/067035, filed Oct. 29, 2015), BT1718 is approximately ten-fold more active in an in vitro cytotoxicity assay (BT1718 $IC_{50}$=1.0 nM versus BT1721 $IC_{50}$=8.9 nM) where the in vitro cytotoxicity=$IC_{50}$ (nM) measured in ATP endpoint assay after 72 hours incubation with HT-1080 cells. Further, BT1721 dosed at 10 mg/kg thrice weekly (tiw) did not show any inhibitory effect on tumor growth in a cell-derived xenograft model in mice implanted with MT1-positive EBC-1 cells whereas BT1718 dosed at 10 mg/kg tiw showed complete tumor clearance. While not being bound by any particular theory, it is believed that this demonstrates the importance of the release characteristics of the linkage for efficacy.

As defined above and described herein, the present invention provides a method of treating cancer, comprising administering to a patient in need thereof a therapeutically effective amount of BT1718, or a pharmaceutically acceptable salt and/or composition thereof. In some embodiments, the cancer is a solid tumor. In some embodiments, the cancer is associated with MT1-MMP.

In some embodiments, the present invention provides a method of treating a sarcoma, comprising administering to a patient in need thereof a therapeutically effective amount of BT1718, or a pharmaceutically acceptable salt and/or composition thereof. In some embodiments, the present invention provides a method of treating a fibrosarcoma, comprising administering to a patient in need thereof a therapeutically effective amount of BT1718, or a pharmaceutically acceptable salt and/or composition thereof. In some embodiments, the present invention provides a method of treating an N-ras mutant/IDH1 mutant soft tissue sarcoma (STS), comprising administering to a patient in need thereof a therapeutically effective amount of BT1718, or a pharmaceutically acceptable salt and/or composition thereof.

In some embodiments, the present invention provides a method of treating lung cancer, comprising administering to a patient in need thereof a therapeutically effective amount of BT1718, or a pharmaceutically acceptable salt and/or composition thereof. In some embodiments, the present invention provides a method of treating met-amplified squamous NSCLC, comprising administering to a patient in need thereof a therapeutically effective amount of BT1718, or a pharmaceutically acceptable salt and/or composition thereof. In some embodiments, the present invention provides a method of treating a squamous cell NSCLC with wild type EGFR, comprising administering to a patient in need thereof a therapeutically effective amount of BT1718, or a pharmaceutically acceptable salt and/or composition thereof. In some embodiments, the present invention provides a method of treating a T790M EGFR-expressing lung adenocarcinoma, comprising administering to a patient in need thereof a therapeutically effective amount of BT1718, or a pharmaceutically acceptable salt and/or composition thereof.

In some embodiments, the present invention provides a method of treating breast cancer, comprising administering to a patient in need thereof a therapeutically effective amount of BT1718, or a pharmaceutically acceptable salt and/or composition thereof. In some embodiments, the present invention provides a method of treating triple negative breast cancer, comprising administering to a patient in need thereof a therapeutically effective amount of BT1718, or a pharmaceutically acceptable salt and/or composition thereof. In some embodiments, the present invention provides a method of treating basaloid triple negative breast cancer, comprising administering to a patient in need thereof a therapeutically effective amount of BT1718, or a pharmaceutically acceptable salt and/or composition thereof.

In some embodiments, the present invention provides a method of treating colon cancer, comprising administering to a patient in need thereof a therapeutically effective amount of BT1718, or a pharmaceutically acceptable salt and/or composition thereof. In some embodiments, the present invention provides a method of treating a high pgp-expressing colorectal adenocarcinoma, comprising administering to a patient in need thereof a therapeutically effective amount of BT1718, or a pharmaceutically acceptable salt and/or composition thereof. In some embodiments, the present invention provides a method of treating a colorectal adenocarcinoma, comprising administering to a patient in need thereof a therapeutically effective amount of BT1718, or a pharmaceutically acceptable salt and/or composition thereof.

In some embodiments, the present invention provides a method of treating gastric cancer, comprising administering to a patient in need thereof a therapeutically effective amount of BT1718, or a pharmaceutically acceptable salt and/or composition thereof. In some embodiments, the present invention provides a method of treating a FGFR-amplified gastric cancer, comprising administering to a patient in need thereof a therapeutically effective amount of BT1718, or a pharmaceutically acceptable salt and/or composition thereof.

In some embodiments, the present invention provides a method of treating head and neck cancer, comprising administering to a patient in need thereof a therapeutically effective amount of BT1718, or a pharmaceutically acceptable salt and/or composition thereof. In some embodiments, the present invention provides a method of treating a nasal septum squamous cell carcinoma, comprising administering to a patient in need thereof a therapeutically effective amount of BT1718, or a pharmaceutically acceptable salt and/or composition thereof.

In some embodiments, the amount administered to the patient of BT1718, or a pharmaceutically acceptable salt thereof, is a minimally effective dose that is <3 mg/kg, wherein the minimally effective dose leads to tumor-stasis when administered intravenous twice a week (IV BIW), or a pharmaceutically acceptable salt thereof. In some embodiments, the amount administered to the patient of BT1718, or a pharmaceutically acceptable salt and/or composition thereof, is a minimally effective dose that is <10 mg/kg, wherein the minimally effective dose leads to tumor-stasis when administered IV BIW, or a pharmaceutically acceptable salt and/or composition thereof. In some embodiments, the amount administered to the patient of BT1718, or a pharmaceutically acceptable salt and/or composition thereof, is a minimally effective dose that is 3 mg/kg, wherein the minimally effective dose leads to tumor-stasis when administered IV BIW, or a pharmaceutically acceptable salt and/or composition thereof. In some embodiments, the amount administered to the patient of BT1718, or a pharmaceutically acceptable salt and/or composition thereof, is a minimally effective dose that is 10 mg/kg, wherein the minimally effective dose leads to tumor-stasis when administered IV BIW, or a pharmaceutically acceptable salt and/or composition thereof.

Pharmaceutically Acceptable Compositions

According to another embodiment, the invention provides a composition comprising BT1718, or a pharmaceutically acceptable salt thereof, and a pharmaceutically acceptable carrier, adjuvant, or vehicle.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of BT1718, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight poletylene glycols and the like.

BT1718, or a pharmaceutically acceptable salt thereof, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

EXEMPLIFICATION

The following Examples illustrate the invention described above; they are not, however, intended to limit the scope of the invention in any way. The beneficial effects of the pharmaceutical compounds, combinations, and compositions of the present invention can also be determined by other test models known as such to the person skilled in the pertinent art.

Example 1

Evaluation of the Efficacy of BT1718 in EBC-1 Xenograft Model in Female BALB/C Nude Mice Study Objective The objective of this study was to evaluate the anti-tumor efficacy of BT1718 in EBC-1 xenograft model in female BALB/c nude mice.

TABLE 2

Experimental Design

| Gr | n | Treatment | Dose (mg/kg) | Dose volume (ml/kg) | Conc. (mg/ml) | Dosing Route | Schedule* |
|----|---|-----------|--------------|---------------------|---------------|--------------|-----------|
| 1 | 3 | Vehicle | — | 10 | — | IV | tiw * 2 weeks |
| 2 | 3 | BT1718 | 30 | 10 | 3 | IV | qw * 2 weeks |
| 3 | 3 | BT1718 | 15 | 10 | 1.5 | IV | biw * 2 weeks |
| 4 | 3 | BT1718 | 10 | 10 | 1 | IV | tiw * 2 weeks |
| 5 | 3 | BT1718 | 4.3 | 10 | 0.43 | IV | qd * 2 weeks |
| 6 | 3 | BT1718 | 9 | 10 | 0.9 | IV | qw * 2 weeks |
| 7 | 3 | BT1718 | 4.5 | 10 | 0.45 | IV | biw * 2 weeks |
| 8 | 3 | BT1718 | 3 | 10 | 0.3 | IV | tiw * 2 weeks |
| 9 | 3 | BT1718 | 1.3 | 10 | 0.13 | IV | qd * 2 weeks |

Note:
n: animal number;
Dosing volume: adjust dosing volume based on body weight 10 µl/g;
*Schedule: tiw = 3 times per week;
qw = 1 time per week;
biw = 2 times per week;
qd = once a day.

Materials
Animals and Housing Condition
Animals
Species: *Mus Musculus*
Strain: Balb/c nude
Age: 6-8 weeks
Sex: female
Body weight: 18-22 g
Number of animals: 27 mice plus spare
Animal supplier: Shanghai SLAC Laboratory Animal Co., LTD.
Housing Condition
The mice were kept in individual ventilation cages at constant temperature and humidity with 3 animals in each cage.
Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, date received, treatment, study number, group number and the starting date of the treatment.
Animal identification: Animals were marked by ear coding.
Test and Positive Control Articles
Product identification: BT1718
Manufacturer: Bicycle Therapeutics
Lot number: N/A
Physical description: Clear solution (in DMSO)
Molecular weight: 3511.4, Formula weight: 3511.4, Purity: >95%
Package and storage condition: stored at −80° C.
Experimental Methods and Procedures
Cell Culture
The EBC-1 tumor cells were maintained in vitro as a monolayer culture in EMEM medium supplemented with 10% heat inactivated fetal bovine serum at 37° C. in an atmosphere of 5% $CO_2$ in air. The tumor cells will be routinely subcultured twice weekly by trypsin-EDTA treatment. The cells growing in an exponential growth phase will be harvested and counted for tumor inoculation.
Tumor Inoculation
Each mouse was inoculated subcutaneously at the right flank with EBC-1 tumor cells ($10 \times 10^6$) in 0.2 ml of PBS for tumor development. The animals were randomized and treatment was started when the average tumor volume reaches approximately 165 $mm^3$ for the efficacy study. The test article administration and the animal numbers in each group are shown in Table 2.

Observations
All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.
Tumor Measurements and the Endpoints
The major endpoint was to see if the tumor growth could be delayed or mice could be cured. Tumor size was measured three times weekly in two dimensions using a caliper, and the volume was expressed in $mm^3$ using the formula: $V = 0.5 \ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.
TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.
Statistical Analysis
Summary statistics, including mean and the standard error of the mean (SEM), are provided for the tumor volume of each group at each time point.
Statistical analysis of difference in tumor volume among the groups was conducted on the data obtained at the best therapeutic time point after the final dose.
A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P < 0.05$ was considered to be statistically significant.
Results
Mortality, Morbidity, and Body Weight Gain or Loss
Animal body weight was monitored regularly as an indirect measure of toxicity. Body weight change in female BALB/c nude mice bearing EBC-1 dosed with BT1718 is shown in Tables 3 and 4. Mice treated with BT1718 at 30 mg/kg qw showed marked body weight loss. Mice in other groups maintained their bodyweight well.

TABLE 3

| | Body Weight (g) | | | | | | | | | |
| --- | --- | --- | --- | --- | --- | --- | --- | --- | --- | --- |
| | Days after the start of treatment | | | | | | | | | |
| Group | 0 | 2 | 4 | 7 | 9 | 11 | 14 | 16 | 18 | 21 |
| Vehicle, tiw | 24.7 ± 0.6 | 24.3 ± 0.7 | 24.5 ± 0.6 | 24.7 ± 0.5 | 25.2 ± 0.6 | 25.7 ± 0.6 | 26.2 ± 0.7 | | | |
| BT1718, 30 mpk, qw | 24.6 ± 0.6 | 20.9 ± 0.3 | 21.9 ± 1.0 | 23.1 ± 1.0 | 20.8 ± 1.0 | 22.1 ± 0.9 | 24.0 ± 1.0 | | | |

TABLE 3-continued

Body Weight (g)

| Group | Days after the start of treatment | | | | | | | | | |
|---|---|---|---|---|---|---|---|---|---|---|
| | 0 | 2 | 4 | 7 | 9 | 11 | 14 | 16 | 18 | 21 |
| BT1718, 15 mpk, biw | 23.7 ± 0.3 | 22.7 ± 0.4 | 22.6 ± 0.3 | 22.8 ± 0.4 | 22.7 ± 0.2 | 23.4 ± 0.3 | 23.7 ± 0.5 | | | |
| BT1718, 10 mpk, tiw | 24.2 ± 0.4 | 23.2 ± 0.6 | 23.7 ± 0.5 | 22.7 ± 0.6 | 23.1 ± 0.4 | 22.9 ± 0.6 | 23.8 ± 0.5 | | | |
| BT1718, 4.3 mpk, qd | 24.8 ± 0.4 | 23.9 ± 0.5 | 23.6 ± 0.8 | 23.7 ± 0.5 | 23.5 ± 0.5 | 24.7 ± 0.7 | 23.5 ± 0.6 | | | |
| BT1718, 9 mpk, qw | 24.0 ± 0.4 | 23.2 ± 0.6 | 23.8 ± 0.5 | 24.7 ± 0.2 | 23.8 ± 0.5 | 24.7 ± 0.4 | 24.9 ± 0.4 | 24.6 ± 0.2 | 24.8 ± 0.2 | 24.8 ± 0.2 |
| BT1718, 4.5 mpk, biw | 24.0 ± 0.6 | 23.4 ± 0.6 | 23.7 ± 0.6 | 24.8 ± 0.7 | 24.2 ± 0.6 | 24.5 ± 0.7 | 25.1 ± 0.6 | 24.7 ± 0.8 | 25.2 ± 0.8 | 25.2 ± 0.7 |
| BT1718, 3 mpk, tiw | 24.0 ± 0.2 | 23.8 ± 0.3 | 24.1 ± 0.3 | 24.5 ± 0.2 | 24.7 ± 0.2 | 24.7 ± 0.2 | 25.1 ± 0.2 | | | |
| BT1718, 1.3 mpk, qd | 25.1 ± 0.3 | 24.6 ± 0.6 | 24.9 ± 0.5 | 24.2 ± 0.5 | 24.5 ± 0.5 | 25.4 ± 0.4 | 25.2 ± 0.8 | | | |

TABLE 4

Body Weight (% Change)

| Group | Days after the start of treatment | | | | | | | | | |
|---|---|---|---|---|---|---|---|---|---|---|
| | 0 | 2 | 4 | 7 | 9 | 11 | 14 | 16 | 18 | 21 |
| Vehicle, tiw | 0.0 | −1.9 ± 1.1 | −0.9 ± 0.6 | −0.3 ± 0.4 | 1.7 ± 0.4 | 3.8 ± 0.2 | 5.8 ± 0.9 | | | |
| BT1718, 30 mpk, qw | 0.0 | −14.9 ± 2.2 | −10.8 ± 4.3 | −6.2 ± 3.5 | −15.5 ± 3.4 | −10.3 ± 3.3 | −2.4 ± 3.2 | | | |
| BT1718, 15 mpk, biw | 0.0 | −4.2 ± 0.6 | −4.5 ± 0.3 | −3.7 ± 2.5 | −4.3 ± 1.7 | −1.2 ± 0.3 | 0.2 ± 1.4 | | | |
| BT1718, 10 mpk, tiw | 0.0 | −4.0 ± 1.3 | −2.1 ± 0.9 | −6.2 ± 0.8 | −4.4 ± 0.3 | −5.2 ± 1.1 | −1.6 0.9 | | | |
| BT1718, 4.3 mpk, qd | 0.0 | −3.4 ± 1.1 | −4.6 ± 2.0 | −4.2 ± 1.3 | −5.2 ± 1.2 | −0.4 ± 1.7 | −5.1 ± 1.9 | | | |
| BT1718, 9mpk, qw | 0.0 | −3.4 ± 0.9 | −0.7 ± 1.8 | 2.8 ± 0.6 | −1.1 ± 0.7 | 2.8 ± 0.9 | 3.7 ± 0.8 | 2.3 ± 0.6 | 3.2 ± 0.8 | 3.1 ± 1.0 |
| BT1718, 4.5 mpk, biw | 0.0 | −2.2 ± 1.0 | −1.3 ± 0.7 | 3.3 ± 0.9 | 1.0 ± 0.7 | 2.4 ± 1.1 | 5.0 ± 0.7 | 3.1 ± 1.5 | 5.3 ± 1.6 | 5.2 ± 1.4 |
| BT1718, 3 mpk, tiw | 0.0 | −1.0 ± 0.9 | 0.3 ± 0.7 | 2.0 ± 0.2 | 2.8 ± 0.6 | 3.1 ± 1.0 | 4.6 ± 1.5 | | | |
| BT1718, 1.3 mpk, qd | 0.0 | −2.0 ± 2.6 | −0.8 ± 1.7 | −3.5 ± 1.3 | −2.2 ± 2.0 | 1.3 ± 1.4 | 0.5 ± 3.2 | | | |

Tumor Volume Trace

Mean tumor volume over time in female Balb/c nude mice bearing EBC-1 xenograft is shown in Table 5.

TABLE 5

The tumor volume trace over time

| Group | Days after the start of treatment | | | | | | | | | |
|---|---|---|---|---|---|---|---|---|---|---|
| | 0 | 2 | 4 | 7 | 9 | 11 | 14 | 16 | 18 | 21 |
| Vehicle, tiw | 162 ± 18 | 298 ± 39 | 455 ± 69 | 669 ± 88 | 841 ± 99 | 1010 ± 130 | 1249 ± 172 | | | |
| BT1718, 30 mpk, qw | 166 ± 10 | 166 ± 22 | 128 ± 6 | 89 ± 4 | 47 ± 3 | 18 ± 2 | 0 ± 0 | | | |
| BT1718, 15 mpk, biw | 161 ± 12 | 173 ± 11 | 136 ± 10 | 79 ± 1 | 36 ± 2 | 12 ± 0 | 0 ± 0 | | | |
| BT1718, 10 mpk, tiw | 167 ± 11 | 216 ± 21 | 205 ± 24 | 114 ± 10 | 45 ± 4 | 16 ± 3 | 0 ± 0 | | | |
| BT1718, 4.3 mpk, qd | 165 ± 18 | 209 ± 7 | 154 ± 10 | 81 ± 3 | 39 ± 3 | 6 ± 3 | 0 ± 0 | | | |

TABLE 5-continued

The tumor volume trace over time

| | Days after the start of treatment | | | | | | | | | |
|---|---|---|---|---|---|---|---|---|---|---|
| Group | 0 | 2 | 4 | 7 | 9 | 11 | 14 | 16 | 18 | 21 |
| BT1718, 9 mpk, qw | 163 ± 19 | 182 ± 25 | 200 ± 28 | 202 ± 64 | 187 ± 70 | 164 ± 61 | 154 ± 72 | 186 ± 83 | 245 ± 119 | 320 ± 153 |
| BT1718, 4.5 mpk, biw | 161 ± 21 | 239 ± 15 | 276 ± 28 | 296 ± 29 | 285 ± 19 | 254 ± 46 | 285 ± 49 | 331 ± 60 | 409 ± 97 | 526 ± 95 |
| BT1718, 3 mpk, tiw | 165 ± 13 | 251 ± 18 | 381 ± 26 | 501 ± 41 | 525 ± 40 | 540 ± 46 | 644 ± 56 | | | |
| BT1718, 1.3 mpk, qd | 161 ± 22 | 204 ± 30 | 243 ± 36 | 278 ± 35 | 326 ± 46 | 370 ± 40 | 473 ± 44 | | | |

Tumor Growth Inhibition Analysis

Tumor growth inhibition rate for BT1718 in the EBC-1 xenograft model was calculated based on tumor volume measurements at day 14 after the start of treatment. The results are displayed in Table 6.

TABLE 6

Tumor growth inhibition analysis (T/C and TGI)

| Gr | Treatment | Tumor Size (mm$^3$)$^a$ | T/C$^b$ (%) | TGI (%) | P value |
|---|---|---|---|---|---|
| 1 | Vehicle, tiw | 1249 ± 172 | — | — | — |
| 2 | BT1718, 30 mpk, qw | 0 ± 0 | 0 | 115 | p < 0.001 |
| 3 | BT1718, 15 mpk, biw | 0 ± 0 | 0 | 115 | p < 0.001 |
| 4 | BT1718, 10 mpk, tiw | 0 ± 0 | 0 | 115 | p < 0.001 |
| 5 | BT1718, 4.3 mpk, qd | 0 ± 0 | 0 | 115 | p < 0.001 |
| 6 | BT1718, 9 mpk, qw | 154 ± 72 | 12 | 101 | p < 0.001 |
| 7 | BT1718, 4.5 mpk, biw | 285 ± 49 | 23 | 89 | p < 0.001 |
| 8 | BT1718, 3 mpk, tiw | 644 ± 56 | 52 | 56 | p < 0.001 |
| 9 | BT1718, 1.3 mpk, qd | 473 ± 44 | 38 | 71 | p < 0.001 |

$^a$Mean ± SEM.
$^b$Tumor Growth Inhibition is calculated by dividing the group average tumor volume for the treated group by the group average tumor volume for the control group (T/C). For a test article to be considered to have anti-tumor activity, T/C must be 50% or less.

Results Summary and Discussion

In this study, the therapeutic efficacy of BT1718 in the EBC-1 xenograft model was evaluated. The measured body weight and body weight changes are shown in the Tables 3 and 4. Tumor sizes of all treatment groups at various time points are shown in Tables 5 and 6.

The mean tumor size of Vehicle treated mice reached 1249 mm$^3$ on day 14, mice treated with BT1718 at 30 mg/kg qw (TGI=115%), 15 mg/kg biw (TGI=115%), 10 mg/kg tiw (TGI=115%), 4.3 mg/kg qd (TGI=115%), 9 mg/kg qw (TGI=101%), 4.5 mg/kg biw (TGI=89%), 3 mg/kg tiw (TGI=56%) and 1.3 mg/kg qd (TGI=71%) showed significant tumor growth inhibition effect. Among them, mice treated with BT1718 at 30 mg/kg qw, 15 mg/kg biw, 10 mg/kg tiw and 4.3 mg/kg qd completely regressed the tumor by day 14, the therapeutic efficacy of BT1718 at 30 mg/kg qw was accompanied by severe body weight loss.

Post-treatment monitoring of the BT1718 18, 9 mg/kg qw group and the 4.5 mg/kg biw group showed re-growth after dosing cessation.

Example 2

In Vivo Efficacy Test of BT1718 in Treatment of HT1080, NCI-11292, NCI-H1975, MDA-MB-231, HCC1806, RPMI2650, HCT-15, HT-29 and SNU-16 Xenograft in BALB/C Nude Mice Study Objective The objective of this study was to evaluate the in vivo anti-tumor efficacy of BT1718 in treatment of HT1080, NCI-H292, NCI-H1975, MDA-MB-231, HCC1806, RPMI2650, HCT-15, HT-29 and SNU-16 xenograft in BALB/c nude mice.

TABLE 7

Experimental Design for HT1080 Study

| Group | n | Treatment | Dosage (mg/kg) | Dosing Volume (ml/g) | Dosing Route | Schedule |
|---|---|---|---|---|---|---|
| 1 | 3 | Vehicle | — | 10 | i.v. | qw |
| 2 | 3 | BT1718 | 1 | 10 | i.v. | qw |
| 3 | 3 | BT1718 | 3 | 10 | i.v. | qw |
| 4 | 3 | BT1718 | 10 | 10 | i.v. | qw |
| 5 | 3 | BT1718 | 1 | 10 | i.v. | biw |
| 6 | 3 | BT1718 | 3 | 10 | i.v. | biw |
| 7 | 3 | BT1718 | 10 | 10 | i.v. | biw |

*The study design was applied to HT1080 study.

TABLE 8

Experimental Design for NCI-H292, NCI-H1975, MDA-MB-231, HCC1806, RPMI2650, HCT-15, HT-29 and SNU-1 Studies

| Group | n | Treatment | Dosage (mg/kg) | Dosing Volume (ml/g) | Dosing Route | Schedule |
|---|---|---|---|---|---|---|
| 1 | 3 | Vehicle | — | 10 | i.v. | biw |
| 2 | 3 | BT1718 | 1 | 10 | i.v. | biw |
| 3 | 3 | BT1718 | 3 | 10 | i.v. | biw |
| 4 | 3 | BT1718 | 10 | 10 | i.v. | biw |

*The study design was applied to NCI-H292, NCI-H1975, MDA-MB-231, HCC1806, RPMI2650, HCT-15, HT-29 and SNU-1 study.

Materials
Animals and Housing Condition
  3.1.1. Animals
    Species: *Mus Musculus*
    Strain: Balb/c nude Age: 6-8 weeks
Sex: female
Body weight: 18-22 g
Number of animals: 117 mice plus spare
Animal supplier: Shanghai SLAC Laboratory Animal Co., LTD.

3.1.2. Housing condition

The mice were kept in individual ventilation cages at constant temperature and humidity with 3 animals in each cage.

Temperature: 20~26° C.
Humidity 40-70%.
Cages: Made of polycarbonate. The size is 300 mm×180 mm×150 mm. The bedding material is corn cob, which is changed twice per week.
Diet: Animals had free access to irradiation sterilized dry granule food during the entire study period.
Water: Animals had free access to sterile drinking water.
Cage identification: The identification labels for each cage contained the following information: number of animals, sex, strain, date received, treatment, study number, group number and the starting date of the treatment.
Animal identification: Animals were marked by ear coding.

Test and Positive Control Articles
Product identification: BT1718
Manufacturer: Bicycle Therapeutics
Lot number: N/A
Physical description: Lyophilised powder
Molecular weight: 3511.408, Formula weight: 3511.408, Purity: >95%
Package and storage condition: stored at −80° C.

Experimental Methods and Procedures

Cell Culture

The HT1080, NCI-H292, NCI-H1975, MDA-MB-231, HCC1806, RPMI2650, HCT-15, HT-29 and SNU-16 tumor cells were maintained in vitro as a monolayer culture in medium supplemented with 10% heat inactivated fetal bovine serum at 37° C. in an atmosphere. The tumor cells will be routinely subcultured twice weekly by trypsin-EDTA treatment. The cells growing in an exponential growth phase will be harvested and counted for tumor inoculation.

Tumor Inoculation

Mouse was inoculated subcutaneously at the right flank with tumor cells for tumor development. The animals were randomized and treatment was started when the average tumor reaches certain volume for the efficacy study, the inoculating cell amounts and starting tumor size were shown as below in Table 9. The test article administration and the animal numbers in each group were shown in the experimental design in Table 10.

TABLE 10

Testing Article Formulation Preparation

| Test article | Concentration (mg/ml) | DMSO stock (20 mg/ml) | Formulation Buffer | Formulation Buffer |
|---|---|---|---|---|
| BT1718 | 0.1 | 4.5 ul | 895.5 ul | 25 mM |
|  | 0.3 | 13.5 ul | 886.5 ul | Histidine pH 7, |
|  | 1 | 45 ul | 855 ul | 10% Sucrose |

Observations

All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured three times weekly in two dimensions using a caliper, and the volume was expressed in mm$^3$ using the formula: V=0.5 a×b$^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Sample Collection

For each model, 3 tumors were collected and snap frozen at the start of study.

Tumors were collected from following animals and fixed in 10% NBF for 24 hr, then transferred into 70% alcohol for potential IHC analysis.

TABLE 9

Inoculating Cell Amounts and Starting Tumor Size

| Cell line | HT1080 | NCI-H292 | NCI-H1975 | MDA-MB-231 | HCC1806 | RPMI2650 | HCT-15 | HT-29 | SNU-16 |
|---|---|---|---|---|---|---|---|---|---|
| Tumor Type | Sarcoma | NSCLC | NSCLC | Breast | Breast | nasal | Colorectal | Colorectal | Gastric |
| Injected Number | 5 × 10$^6$ | 10 × 10$^6$ | 10 × 10$^6$ | 10 × 10$^6$ | 5 × 10$^6$ | 10 × 10$^6$ | 10 × 10$^6$ | 5 × 10$^6$ | 10 × 10$^6$ |
| Matrigel | − | − | − | + | + | + | − | − | + |
| Tumor volume | 180 mm$^3$ | 150 mm$^3$ | 170 mm$^3$ | 187 mm$^3$ | 189 mm$^3$ | 147 mm$^3$ | 157 mm$^3$ | 160 mm$^3$ | 160 mm$^3$ |

TABLE 11

| Cell line | Animal ID | Treatment |
|---|---|---|
| HT-29 | 1-1 | Vehicle |
|  | 1-2 | Vehicle |
|  | 1-3 | Vehicle |
|  | 2-1 | BT1718, 1 mpk, biw |
|  | 2-2 | BT1718, 1 mpk, biw |
|  | 2-3 | BT1718, 1 mpk, biw |
| HT1080 | 4-3 | BT1718, 10 mpk, qw |
|  | 6-1 | BT1718, 3 mpk, biw |
|  | 6-2 | BT1718, 3 mpk, biw |
|  | 6-3 | BT1718, 3 mpk, biw |
| MDA-MB-231 | 4-1 | BT1718, 10 mpk, biw |
|  | 4-2 | BT1718, 10 mpk, biw |
|  | 4-3 | BT1718, 10 mpk, biw |
| NCI-H292 | 4-1 | BT1718, 10 mpk, biw |
|  | 4-2 | BT1718, 10 mpk, biw |
| RPMI2650 | 4-1 | BT1718, 10 mpk, biw |
|  | 4-2 | BT1718, 10 mpk, biw |
|  | 4-3 | BT1718, 10 mpk, biw |

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant.

Results

Mortality, Morbidity, and Body Weight Gain or Loss

Animal body weight was monitored regularly as an indirect measure of toxicity. Body weight changes in female BALB/c nude mice bearing tumors dosed with BT1718 are shown in Tables 12-20.

TABLE 12

Body Weight (g) in HT1080 Study

| Group | Treatment | Days after the start of treatment | | | | | | |
|---|---|---|---|---|---|---|---|---|
|  |  | 0 | 2 | 4 | 7 | 9 | 11 | 14 |
| 1 | Vehicle, biw | 22.2 ± 1.0 | 21.6 ± 1.3 | 21.3 ± 1.0 | 21.8 ± 0.9 | 21.6 ± 0.8 | 20.0 ± 0.8 | 19.9 ± 1.0 |
| 2 | BT1718 1 mpk, qw | 22.5 ± 0.6 | 22.2 ± 0.5 | 22.6 ± 0.5 | 22.3 ± 0.3 | 22.2 ± 0.3 | 20.5 ± 0.3 | 19.6 ± 0.2 |
| 3 | BT1718 3 mpk, qw | 22.6 ± 0.3 | 21.4 ± 0.2 | 21.8 ± 0.8 | 22.0 ± 1.1 | 21.3 ± 0.7 | 21.4 ± 0.5 | 21.0 ± 0.6 |
| 4 | BT1718 10 mpk, qw | 22.6 ± 1.2 | 21.1 ± 1.2 | 22.1 ± 1.2 | 23.2 ± 1.0 | 22.7 ± 1.1 | 23.8 ± 1.3 | 24.8 ± 1.5 |
| 5 | BT1718 1 mpk, biw | 22.7 ± 0.5 | 22.2 ± 0.4 | 22.3 ± 0.2 | 22.2 ± 0.2 | 21.5 ± 0.2 | 20.1 ± 0.1 | 19.4 ± 0.0 |
| 6 | BT1718 3 mpk, biw | 23.1 ± 0.6 | 22.8 ± 0.9 | 22.5 ± 0.7 | 23.4 ± 0.8 | 24 ± 1.1 | 24.5 ± 0.9 | 24.7 ± 0.9 |
| 7 | BT1718 10 mpk, biw | 22.5 ± 1.0 | 21.8 ± 1.2 | 21.8 ± 1.1 | 22.7 ± 0.9 | 22.1 ± 0.9 | 22 ± 1.1 | 22.6 ± 1.0 |

TABLE 13

Body Weight (g) in NCI-H292 Study

| Group | Treatment | Days after the start of treatment | | | | | | |
|---|---|---|---|---|---|---|---|---|
|  |  | 0 | 2 | 4 | 7 | 9 | 11 | 14 |
| 1 | Vehicle, biw | 22.6 ± 0.6 | 23.0 ± 0.6 | 23.3 ± 1.0 | 23.6 ± 1.0 | 23.9 ± 0.9 | 23.3 ± 0.7 | 23.0 ± 0.5 |
| 2 | BT1718 1 mpk, biw | 22.8 ± 0.7 | 22.9 ± 0.3 | 23.4 ± 0.5 | 23.6 ± 0.6 | 23.7 ± 0.7 | 23.4 ± 0.7 | 23.5 ± 1.0 |
| 3 | BT1718 3 mpk, biw | 22.7 ± 0.5 | 23.5 ± 0.4 | 23.2 ± 0.7 | 23.4 ± 0.8 | 22.9 ± 0.9 | 22.6 ± 1.0 | 22.0 ± 1.2 |
| 4 | BT1718 10 mpk, biw | 22.8 ± 0.4 | 22.1 ± 0.3 | 21.7 ± 0.3 | 22.4 ± 0.3 | 21.8 ± 0.2 | 21.8 ± 0.2 | 22.5 ± 0.4 |

TABLE 14

Body Weight (g) in NCI-H1975 Study

| Group | Treatment | Days after the start of treatment | | | | | | |
|---|---|---|---|---|---|---|---|---|
|  |  | 0 | 2 | 4 | 7 | 9 | 11 | 14 |
| 1 | Vehicle, biw | 23.2 ± 0.7 | 23.3 ± 1.1 | 23.4 ± 1.6 | 23.7 ± 1.8 | 24.1 ± 1.9 | 24.2 ± 2.2 | 24.7 ± 2.0 |
| 2 | BT1718 1 mpk, biw | 23.9 ± 0.7 | 23.5 ± 0.7 | 24.0 ± 0.9 | 24.4 ± 0.7 | 24.6 ± 0.8 | 25.2 ± 1.1 | 26.0 ± 1.0 |

TABLE 14-continued

Body Weight (g) in NCI-H1975 Study

| | | Days after the start of treatment | | | | | | |
|---|---|---|---|---|---|---|---|---|
| Group | Treatment | 0 | 2 | 4 | 7 | 9 | 11 | 14 |
| 3 | BT1718 3 mpk, biw | 23.6 ± 0.4 | 23.6 ± 0.5 | 24.0 ± 0.8 | 24.8 ± 0.8 | 24.4 ± 0.9 | 25.1 ± 0.8 | 25.0 ± 0.7 |
| 4 | BT1718 10 mpk, biw | 23.3 ± 1.4 | 22.5 ± 1.7 | 22.4 ± 1.7 | 22.6 ± 1.9 | 22.4 ± 1.8 | 22.3 ± 1.9 | 22.7 ± 2.0 |

TABLE 15

Body Weight (g) in MDA-MB-231 Study

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 23.2 ± 1.1 | 23.0 ± 1.4 | 23.7 ± 1.1 | 24.2 ± 1.2 | 24.9 ± 0.8 | 25.2 ± 1.0 | 25.7 ± 0.9 |
| 2 | BT1718 1 mpk, biw | 23.4 ± 0.5 | 23.3 ± 0.6 | 23.3 ± 0.6 | 24.6 ± 0.5 | 24.6 ± 0.6 | 24.1 ± 0.1 | 24.9 ± 0.5 |
| 3 | BT1718 3 mpk, biw | 23.0 ± 0.9 | 22.5 ± 1.0 | 22.3 ± 1.0 | 23.8 ± 1.1 | 23.8 ± 1.1 | 23.6 ± 1.1 | 23.9 ± 1.3 |
| 4 | BT1718 10 mpk, biw | 23.3 ± 1.0 | 22.9 ± 1.3 | 22.2 ± 0.9 | 23.3 ± 1.2 | 23.0 ± 1.1 | 21.6 ± 1.0 | 24.3 ± 1.1 |

TABLE 16

Body Weight (g) in HCC1806 Study

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 22.6 ± 0.3 | 23.3 ± 0.4 | 23.8 ± 0.3 | 23.8 ± 0.5 | 23.9 ± 0.5 | 23.7 ± 0.7 | 23.7 ± 1.2 |
| 2 | BT1718 1 mpk, biw | 22.5 ± 0.7 | 22.8 ± 0.7 | 23.6 ± 0.6 | 24.2 ± 0.5 | 24.0 ± 0.5 | 24.3 ± 0.6 | 24.8 ± 0.4 |
| 3 | BT1718 3 mpk, biw | 22.6 ± 1.0 | 23.2 ± 0.9 | 22.6 ± 1.0 | 22.8 ± 1.4 | 22.6 ± 1.6 | 23.2 ± 1.2 | 23.5 ± 1.1 |
| 4 | BT1718 10 mpk, biw | 23.1 ± 0.6 | 22.2 ± 1.1 | 23.2 ± 0.9 | 23.4 ± 0.8 | 22.9 ± 1.0 | 22.5 ± 1.2 | 23.8 ± 0.7 |

TABLE 17

Body Weight (g) in RPMI2650 Study

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 22.1 ± 0.4 | 22.1 ± 0.5 | 22.4 ± 0.5 | 22.9 ± 0.5 | 22.6 ± 0.2 | 22.4 ± 0.2 | 22.7 ± 0.5 |
| 2 | BT1718 1 mpk, biw | 21.8 ± 0.5 | 22.1 ± 0.6 | 22.1 ± 0.7 | 22.6 ± 0.5 | 22.8 ± 0.5 | 22.6 ± 0.6 | 23.1 ± 0.8 |
| 3 | BT1718 3 mpk, biw | 22.1 ± 0.7 | 21.9 ± 0.8 | 21.4 ± 0.6 | 21.9 ± 0.8 | 21.4 ± 0.7 | 20.7 ± 0.8 | 21.0 ± 0.7 |
| 4 | BT1718 10 mpk, biw | 22.0 ± 0.3 | 21.2 ± 0.1 | 20.6 ± 0.5 | 21.1 ± 0.4 | 19.9 ± 0.3 | 19.2 ± 0.3 | 19.6 ± 0.7 |

TABLE 18

Body Weight (g) in HCT-15 Study

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 21.8 ± 0.3 | 22.0 ± 0.2 | 21.9 ± 0.3 | 22.0 ± 0.3 | 22.1 ± 0.4 | 22.2 ± 0.5 | 23.5 ± 0.8 |
| 2 | BT1718 1 mpk, biw | 22.2 ± 0.5 | 21.8 ± 0.3 | 21.6 ± 0.6 | 22.3 ± 0.5 | 21.9 ± 0.3 | 21.9 ± 0.5 | 22.1 ± 0.5 |

TABLE 18-continued

Body Weight (g) in HCT-15 Study

| | | Days after the start of treatment | | | | | | |
|---|---|---|---|---|---|---|---|---|
| Group | Treatment | 0 | 2 | 4 | 7 | 9 | 11 | 14 |
| 3 | BT1718 3 mpk, biw | 21.6 ± 0.5 | 21.4 ± 0.2 | 21.6 ± 0.2 | 22.7 ± 0.4 | 22.2 ± 0.4 | 22.2 ± 0.5 | 22.3 ± 0.6 |
| 4 | BT1718 10 mpk, biw | 22.2 ± 0.3 | 21.2 ± 0.2 | 20.2 ± 0.5 | 21.7 ± 0.3 | 19.9 ± 0.3 | 20.3 ± 0.7 | 20.8 ± 0.8 |

TABLE 19

Body Weight (g) in HT-29 Study

| | | Days after the start of treatment | | | | | | |
|---|---|---|---|---|---|---|---|---|
| Group | Treatment | 0 | 2 | 4 | 6 | 8 | 11 | 13 |
| 1 | Vehicle, biw | 23.0 ± 0.2 | 23.0 ± 0.2 | 22.9 ± 0.1 | 22.9 ± 0.3 | 22.9 ± 0.3 | 22.6 ± 0.5 | 22.6 ± 0.8 |
| 2 | BT1718 1 mpk, biw | 23.0 ± 0.2 | 22.8 ± 0.2 | 22.3 ± 0.5 | 22.3 ± 0.5 | 22.3 ± 0.4 | 22.4 ± 0.7 | 22.3 ± 0.7 |
| 3 | BT1718 3 mpk, biw | 22.2 ± 0.2 | 22.1 ± 0.4 | 22.0 ± 0.5 | 22.4 ± 0.6 | 22.6 ± 0.6 | 22.0 ± 0.4 | 22.2 ± 0.3 |
| 4 | BT1718 10 mpk, biw | 24.6 ± 1.2 | 23.6 ± 1.2 | 22.1 ± 1.5 | 22.9 ± 1.5 | 21.2 ± 1.2 | 21.2 ± 1.7 | 21.7 ± 1.0 |

TABLE 20

Body Weight (g) in SNU-16 Study

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, tiw | 22.9 ± 0.9 | 22.9 ± 0.9 | 23.0 ± 0.9 | 23.2 ± 1.0 | 23.1 ± 0.8 | 23.2 ± 0.6 | 22.9 ± 0.2 |
| 2 | Vehicle, biw | 22.9 ± 0.4 | 22.6 ± 0.4 | 22.7 ± 0.2 | 22.8 ± 0.1 | 22.7 ± 0.2 | 23.0 ± 0.5 | 23.4 ± 0.4 |
| 3 | BT1718 1 mpk, biw | 22.9 ± 0.5 | 22.8 ± 0.5 | 23.0 ± 0.5 | 23.0 ± 0.4 | 22.7 ± 0.5 | 23.0 ± 0.5 | 23.3 ± 0.5 |
| 4 | BT1718 3 mpk, biw | 22.7 ± 0.3 | 22.1 ± 0.5 | 21.8 ± 0.2 | 21.5 ± 0.3 | 20.0 ± 0.1 | 20.2 ± 0.6 | 20.6 ± 0.6 |

Tumor Volume Trace

Mean tumor volume over time in female Balb/c nude mice bearing xenograft is shown in Tables 21-29

TABLE 21

HT1080 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 180 ± 12 | 292 ± 34 | 677 ± 125 | 1132 ± 138 | 1470 ± 178 | 1806 ± 64 | 2186 ± 77 |
| 2 | BT1718 1 mpk, qw | 178 ± 4 | 257 ± 26 | 627 ± 112 | 934 ± 176 | 1253 ± 182 | 1593 ± 251 | 1814 ± 320 |
| 3 | BT1718 3 mpk, qw | 179 ± 18 | 191 ± 17 | 183 ± 90 | 218 ± 149 | 266 ± 142 | 254 ± 125 | 306 ± 119 |
| 4 | BT1718 10 mpk, qw | 179 ± 14 | 146 ± 19 | 35 ± 4 | 25 ± 3 | 15 ± 8 | 5 ± 5 | 5 ± 5 |
| 5 | BT1718 1 mpk, biw | 177 ± 6 | 265 ± 33 | 669 ± 107 | 1009 ± 156 | 1318 ± 146 | 1526 ± 160 | 1650 ± 218 |
| 6 | BT1718 3 mpk, biw | 178 ± 15 | 196 ± 16 | 100 ± 10 | 39 ± 8 | 18 ± 10 | 8 ± 8 | 3 ± 3 |
| 7 | BT1718 10 mpk, biw | 180 ± 21 | 182 ± 41 | 58 ± 14 | 32 ± 7 | 27 ± 14 | 26 ± 13 | 20 ± 11 |

TABLE 22

NCI-H292 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 154 ± 6 | 229 ± 16 | 357 ± 26 | 605 ± 71 | 879 ± 86 | 1184 ± 142 | 1442 ± 124 |
| 2 | BT1718 1 mpk, biw | 153 ± 9 | 215 ± 25 | 326 ± 49 | 514 ± 54 | 669 ± 53 | 978 ± 97 | 1174 ± 98 |
| 3 | BT1718 3 mpk, biw | 151 ± 15 | 226 ± 22 | 334 ± 65 | 443 ± 70 | 591 ± 90 | 781 ± 178 | 920 ± 258 |
| 4 | BT1718 10 mpk, biw | 153 ± 6 | 152 ± 8 | 151 ± 32 | 159 ± 49 | 158 ± 49 | 143 ± 52 | 133 ± 44 |

TABLE 23

NCI-H1975 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 170 ± 14 | 221 ± 18 | 381 ± 62 | 619 ± 115 | 830 ± 168 | 1226 ± 108 | 1495 ± 163 |
| 2 | BT1718 1 mpk, biw | 170 ± 9 | 224 ± 33 | 352 ± 69 | 587 ± 134 | 840 ± 155 | 1265 ± 144 | 1455 ± 130 |
| 3 | BT1718 3 mpk, biw | 166 ± 13 | 241 ± 20 | 377 ± 38 | 605 ± 84 | 732 ± 95 | 1095 ± 207 | 1343 ± 349 |
| 4 | BT1718 10 mpk, biw | 168 ± 6 | 209 ± 31 | 269 ± 23 | 419 ± 22 | 442 ± 23 | 442 ± 26 | 421 ± 31 |

TABLE 24

MDA-MB-231 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 188 ± 11 | 292 ± 16 | 468 ± 30 | 696 ± 38 | 887 ± 55 | 1035 ± 65 | 1308 ± 30 |
| 2 | BT1718 1 mpk, biw | 187 ± 6 | 288 ± 25 | 435 ± 25 | 636 ± 53 | 822 ± 117 | 979 ± 51 | 1221 ± 62 |
| 3 | BT1718 3 mpk, biw | 187 ± 11 | 281 ± 23 | 389 ± 21 | 547 ± 38 | 729 ± 74 | 829 ± 79 | 1021 ± 65 |
| 4 | BT1718 10 mpk, biw | 187 ± 10 | 270 ± 25 | 312 ± 27 | 294 ± 31 | 248 ± 23 | 204 ± 19 | 158 ± 20 |

TABLE 25

HCC1806 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 191 ± 17 | 286 ± 42 | 459 ± 62 | 703 ± 95 | 958 ± 177 | 1144 ± 161 | 1264 ± 143 |
| 2 | BT1718 1 mpk, biw | 188 ± 23 | 265 ± 53 | 428 ± 44 | 660 ± 85 | 793 ± 122 | 882 ± 118 | 1169 ± 137 |
| 3 | BT1718 3 mpk, biw | 190 ± 17 | 259 ± 34 | 296 ± 41 | 276 ± 77 | 323 ± 116 | 392 ± 126 | 527 ± 158 |
| 4 | BT1718 10 mpk, biw | 186 ± 30 | 221 ± 35 | 185 ± 20 | 142 ± 9 | 92 ± 2 | 84 ± 6 | 67 ± 11 |

TABLE 26

RPMI2650 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 148 ± 15 | 162 ± 6 | 231 ± 11 | 389 ± 27 | 523 ± 36 | 686 ± 90 | 867 ± 124 |
| 2 | BT1718 1 mpk, biw | 146 ± 5 | 159 ± 9 | 213 ± 23 | 362 ± 34 | 470 ± 68 | 614 ± 96 | 833 ± 126 |

TABLE 26-continued

RPMI2650 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 3 | BT1718 3 mpk, biw | 147 ± 11 | 164 ± 20 | 220 ± 23 | 365 ± 10 | 447 ± 18 | 576 ± 19 | 724 ± 28 |
| 4 | BT1718 10 mpk, biw | 147 ± 7 | 151 ± 10 | 190 ± 25 | 198 ± 38 | 165 ± 42 | 155 ± 54 | 131 ± 49 |

TABLE 27

HCT-15 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, biw | 157 ± 11 | 168 ± 19 | 204 ± 13 | 364 ± 11 | 560 ± 13 | 916 ± 45 | 1229 ± 52 |
| 2 | BT1718 1 mpk, biw | 157 ± 6 | 174 ± 9 | 207 ± 14 | 385 ± 19 | 585 ± 26 | 937 ± 70 | 1238 ± 36 |
| 3 | BT1718 3 mpk, biw | 157 ± 6 | 140 ± 7 | 195 ± 26 | 389 ± 47 | 581 ± 54 | 901 ± 79 | 1180 ± 143 |
| 4 | BT1718 10 mpk, biw | 157 ± 11 | 130 ± 7 | 138 ± 14 | 265 ± 16 | 342 ± 47 | 562 ± 73 | 880 ± 89 |

TABLE 28

HT-29 Tumor Volume Trace over Time

| | | Days after the start of treatment | | | | | | |
|---|---|---|---|---|---|---|---|---|
| Group | Treatment | 0 | 2 | 4 | 6 | 8 | 11 | 13 |
| 1 | Vehicle, biw | 162 ± 33 | 209 ± 37 | 250 ± 50 | 282 ± 54 | 336 ± 70 | 500 ± 71 | 652 ± 143 |
| 2 | BT1718 1 mpk, biw | 160 ± 27 | 189 ± 18 | 203 ± 13 | 260 ± 18 | 273 ± 35 | 453 ± 45 | 533 ± 43 |
| 3 | BT1718 3 mpk, biw | 159 ± 36 | 178 ± 41 | 214 ± 51 | 268 ± 70 | 297 ± 87 | 472 ± 129 | 616 ± 145 |
| 4 | BT1718 10 mpk, biw | 164 ± 32 | 177 ± 28 | 195 ± 36 | 232 ± 54 | 198 ± 44 | 182 ± 46 | 146 ± 32 |

TABLE 29

SNU-16 Tumor Volume Trace over Time

| | | Days after the start of treatment | | | | | | |
|---|---|---|---|---|---|---|---|---|
| Group | Treatment | 0 | 2 | 4 | 7 | 9 | 11 | 14 |
| 1 | Vehicle, tiw | 158 ± 25 | 175 ± 16 | 195 ± 15 | 235 ± 7 | 255 ± 3 | 329 ± 9 | 450 ± 62 |
| 2 | Vehicle, biw | 162 ± 24 | 176 ± 24 | 207 ± 18 | 211 ± 30 | 216 ± 28 | 236 ± 27 | 304 ± 43 |
| 3 | BT1718 1 mpk, biw | 160 ± 24 | 160 ± 15 | 140 ± 12 | 137 ± 13 | 139 ± 9 | 142 ± 11 | 176 ± 9 |
| 4 | BT1718 3 mpk, biw | 161 ± 29 | 115 ± 13 | 36 ± 4 | 25 ± 4 | 18 ± 1 | 5 ± 3 | 0 ± 0 |

Tumor Growth Inhibition Analysis

Tumor growth inhibition rate for BT1718 in the xenograft model was calculated based on tumor volume measurements at day 14 after the start of treatment and shown in Tables 30-38.

TABLE 30

HT1080 Tumor Growth Inhibition Analysis

| Gr | Treatment | Tumor Volume(mm³) | TGI (%) | P value |
|---|---|---|---|---|
| 1 | Vehicle, qw | 2186 ± 77 | — | — |
| 2 | BT1718, 1 mpk, qw | 1814 ± 320 | 18.4 | p > 0.05 |
| 3 | BT1718, 3 mpk, qw | 306 ± 119 | 93.7 | p < 0.001 |
| 4 | BT1718, 10 mpk, qw | 5 ± 5 | 108.7 | p < 0.001 |
| 5 | BT1718, 1 mpk, biw | 1650 ± 218 | 26.5 | p > 0.05 |
| 6 | BT1718, 3 mpk, biw | 3 ± 3 | 108.7 | p < 0.001 |
| 7 | BT1718, 10 mpk, biw | 20 ± 11 | 108.0 | p < 0.001 |

TABLE 31

NCI-H292 Tumor Growth Inhibition Analysis

| Gr | Treatment | Tumor Volume(mm³) | TGI (%) | P value |
|---|---|---|---|---|
| 1 | Vehicle, biw | 1442 ± 124 | — | — |
| 2 | BT1718, 1 mpk, biw | 1174 ± 98 | 20.7 | p > 0.05 |
| 3 | BT1718, 3 mpk, biw | 920 ± 258 | 40.3 | p > 0.05 |
| 4 | BT1718, 10 mpk, biw | 133 ± 44 | 101.6 | p < 0.001 |

TABLE 32

NCI-H1975 Tumor Growth Inhibition Analysis

| Gr | Treatment | Tumor Volume(mm³) | TGI (%) | P value |
|---|---|---|---|---|
| 1 | Vehicle, biw | 1495 ± 163 | — | — |
| 2 | BT1718, 1 mpk, biw | 1455 ± 130 | 3.0 | p > 0.05 |
| 3 | BT1718, 3 mpk, biw | 1343 ± 349 | 11.2 | p > 0.05 |
| 4 | BT1718, 10 mpk, biw | 421 ± 31 | 80.9 | p < 0.05 |

TABLE 33

MDA-MB-231 Tumor Growth Inhibition Analysis

| Gr | Treatment | Tumor Volume(mm³) | TGI (%) | P value |
|---|---|---|---|---|
| 1 | Vehicle, biw | 1308 ± 30 | — | — |
| 2 | BT1718, 1 mpk, biw | 1221 ± 62 | 7.6 | p > 0.05 |
| 3 | BT1718, 3 mpk, biw | 1021 ± 65 | 25.5 | p < 0.01 |
| 4 | BT1718, 10 mpk, biw | 158 ± 20 | 102.6 | p < 0.001 |

TABLE 34

HCC1806 Tumor Growth Inhibition Analysis

| Gr | Treatment | Tumor Volume(mm³) | TGI (%) | P value |
|---|---|---|---|---|
| 1 | Vehicle, biw | 1264 ± 143 | — | — |
| 2 | BT1718, 1 mpk, biw | 1169 ± 137 | 8.6 | p > 0.05 |
| 3 | BT1718, 3 mpk, biw | 527 ± 158 | 68.6 | p < 0.01 |
| 4 | BT1718, 10 mpk, biw | 67 ± 11 | 111.1 | p < 0.001 |

TABLE 35

HCT-15 Tumor Growth Inhibition Analysis

| Gr | Treatment | Tumor Volume(mm³) | TGI (%) | P value |
|---|---|---|---|---|
| 1 | Vehicle, biw | 1229 ± 52 | — | — |
| 2 | BT1718, 1 mpk, biw | 1238 ± 36 | -0.9 | p > 0.05 |
| 3 | BT1718, 3 mpk, biw | 1180 ± 143 | 4.6 | p > 0.05 |
| 4 | BT1718, 10 mpk, biw | 880 ± 89 | 32.5 | p > 0.05 |

TABLE 36

RPMI2650 Tumor Growth Inhibition Analysis

| Gr | Treatment | Tumor Volume(mm³) | TGI (%) | P value |
|---|---|---|---|---|
| 1 | Vehicle, biw | 867 ± 124 | — | — |
| 2 | BT1718, 1 mpk, biw | 833 ± 126 | 4.5 | p > 0.05 |
| 3 | BT1718, 3 mpk, biw | 724 ± 28 | 19.8 | p > 0.05 |
| 4 | BT1718, 10 mpk, biw | 131 ± 49 | 102.1 | p < 0.01 |

TABLE 37

HT-29 Tumor Growth Inhibition Analysis

| Gr | Treatment | Tumor Volume(mm³) | TGI (%) | P value |
|---|---|---|---|---|
| 1 | Vehicle, biw | 652 ± 143 | — | — |
| 2 | BT1718, 1 mpk, biw | 533 ± 43 | 24.0 | p > 0.05 |
| 3 | BT1718, 3 mpk, biw | 616 ± 145 | 6.8 | p > 0.05 |
| 4 | BT1718, 10 mpk, biw | 146 ± 32 | 103.6 | p < 0.05 |

TABLE 38

SNU-16 Tumor Growth Inhibition Analysis

| Gr | Treatment | Tumor Volume(mm³) | TGI (%) | P value |
|---|---|---|---|---|
| 1 | Vehicle, biw | 450 ± 62 | — | — |
| 2 | BT1718, 1 mpk, biw | 304 ± 43 | 51.4 | p > 0.05 |
| 3 | BT1718, 3 mpk, biw | 176 ± 9 | 94.5 | p < 0.01 |
| 4 | BT1718, 10 mpk, biw | 0 ± 0 | 155 | p < 0.001 |

Summary and Discussion

In this study, the therapeutic efficacy of BT1718 in the HT1080, NCI-H292, NCI-H1975, MDA-MB-231, HCC1806, RPMI2650, HCT-15, HT-29 and SNU-16 xenograft models were evaluated. The measured body weights are shown in Tables 12-20. Tumor volumes at various time points are shown in Tables 21-29.

In HT1080 sarcoma xenografts, the tumors completely regressed after 2 weeks BT1718 3 mg/kg biw, 10 mg/kg qw and 10 mg/kg biw treatments. Following cessation of dosing, re-growth to 150 mm3 was seen with 1/3 animals previously treated with 10 mg/kg qw, and 3/3 animals previously treated with 3 mg/kg biw. On re-dosing, 1/3 animals receiving 3 mg/kg biw showed transient response, 3/3 ultimately re-grew despite dosing. The one animal showing relapse at 10 mg/kg qw showed a transient response, before re-growth was seen in weeks 3-4 of re-dosing. Tumors in BT1718 10 mg/kg biw group did not re-grow during the dosing suspension period of 2 months.

Both NCI-H292 and NCI-H1975 NSCLC xenografts regressed to below 50 mm3 after 4 weeks BT1718 10 mg/kg biw treatment. H292 tumors re-grew to 150 mm3 after 2-3 weeks dosing suspension, when the treatments were resumed, 1/3 tumors failed to respond to BT1718 treatment 2/3 showed lack of clear tumor growth on re-treatment; NCI-H1975 study was BT1718 at PG-D40 due to marked body weight lost.

In MDA-MB-231 and HCC1806 breast cancer xenografts, both models regressed to below 50 mm3 after 2-3 weeks BT1718 10 mg/kg biw treatment. MDA-MB-231 tumors re-grew to 150 mm3 after 3 weeks dosing suspension, when the treatments were resumed, the tumors showed slow re-growth during BT1718 treatment. The HCC1806 tumors showed no re-growth during the 2 months dosing suspension period.

In RPMI2650 nasal carcinoma xenografts, BT1718 10 mg/kg biw treatment showed significant tumor inhibition effect, but didn't cause tumor regression. In HT29 colorectal cancer xenografts, BT1718 10 mg/kg biw treatment showed significant tumor inhibition effect, but didn't cause tumor regression. In HCT-15 model, BT1718 treatment did not show obvious anti-tumor activity.

In SNU-16 gastric cancer xenografts, the tumors were completely regressed after 2 weeks BT1718 10 mg/kg biw treatment. After 7 weeks dosing suspension, the tumors re-grew to 150 mm3. When the treatment was resumed, the tumor regression was seen after 1-2 weeks dosing.

Example 3

Evaluation of the Efficacy of BT1718 in a Patient-Derived Xenograft (PDX) Model in Female BALB/C Nude Mice Study Objective The objective of the project is to evaluate the in vivo therapeutic efficacy of test articles in the LU-01-0046 non-small-cell lung carcinoma (NSCLC) PDX model. LU-01-0046 is a high MT1-expressing NSCLC that is docetaxel resistant.

Study Design

The NSCLC PDX model will be used in this study as shown in Table 39.

TABLE 39

NSCLC PDX model used in study

| Model Name | Cancer Type | Tumor growth speed | Array | RSQ | MT1-MMP expression |
|---|---|---|---|---|---|
| LU-01-0046 | NSCLC | Tumor size can reach 1000 mm$^3$ in 40 days after tumor inoculation | 9.88 | 367.003 | High |

Animals

Balb/C nude, female, 6-8 weeks, weighing approximately 18-22 g.

Tumor Inoculation

Each mouse was inoculated subcutaneously at the right flank with certain kind of tumor fragment (30 mm3) for tumor development. The treatments started when the average tumor volume reaches approximately 150-200 mm$^3$. The test article administration and the animal numbers in each group are shown in Table 40 which details the experimental design.

TABLE 40

Study Design

| Group | Treatment | n | Dose (mg/kg) | Dosing Volume (μL/g) | Dosing Route | Schedule |
|---|---|---|---|---|---|---|
| 1 | Vehicle | 6 | — | 10 | iv | biw × 4 wks |
| 2 | BT1718 | 6 | 3 | 10 | iv | biw × 4 wks |
| 3 | BT1718 | 6 | 10 | 10 | iv | biw × 4 wks |
| 4 | Docetaxel | 6 | 20 | 10 | iv | biw × 4 wks |

Treatment was given until the control tumors reached an average of 1000 mm$^3$.

Animal Housing

An acclimation period of approximately one week will be allowed between animal arrival and tumor inoculation in order to accustom the animals to the laboratory environment. The mice will be maintained in a special pathogen-free environment and in individual ventilation cages (3 mice per cage). All cages, bedding, and water will be sterilized before use when working in the mouse room, the investigators will wear lab coat and latex or vinyl gloves. Each cage will be clearly labeled with a cage card indicating number of animals, sex, strain, date received, treatment, study number, group number and the starting date of the treatment The cages with food and water will be changed twice a week. The targeted conditions for animal room environment and photoperiod will be as follows:

Temperature: 20-26° C.
Humidity: 40-70%
Light cycle: 12 hours light and 12 hours dark Dietary Materials All animals will have free access to a standard certified commercial laboratory diet. Maximum allowable concentrations of contaminants in the diet are controlled and routinely analyzed by the manufacturers. Autoclaved municipal tap water suitable for human consumption will be available to the animals ad libitum. It is considered that there are no known contaminants in the dietary materials that could influence the tumor growth Assignment to Groups Before commencement of treatment all animals will be weighed and the tumor volumes will be measured. Since the tumor volume can affect the effectiveness of any given treatment, mice will be assigned into groups using randomized block design based upon their tumor volumes. This ensures that all the groups are comparable at the baseline.

Observations

The protocol and any amendment(s) or procedures involving the care and use of animals in this study will be reviewed and approved prior to conduct. During the study, the care and use of animals will be conducted in accordance with the regulations of the Association for Assessment and Accreditation of Laboratory Animal Care (AAALAC). After inoculation, the animals will be checked daily for morbidity and mortality. At the time of routine monitoring, the animals will be checked for any effects of tumor growth and treatments on normal behavior such as mobility, food and water consumption, body weight gain/loss (body weights will be measured twice weekly), eye/hair matting and any other abnormal effect. Death and observed clinical signs will be recorded on the basis of the numbers of animals within each subset.

Endpoints

The major endpoint is to see if the tumor growth can be delayed or mice can be cured. Tumor sizes will be measured twice weekly in two dimensions using a caliper and the volume will be expressed in mm$^3$ using the formula: $V=0.5 a \times b^2$ where a and b are the long and short diameters of the tumor, respectively. The tumor sizes are then used for the calculations of both T-C and TIC values. T-C is calculated with T as the median time (in days) required for the treatment group tumors to reach a predetermined size (e.g., 1.000 mm$^3$), and C is the median time (in days) for the control group tumors to reach the same size. The TIC value (in percent) is an indication of antitumor effectiveness, T and C are the mean volume of the treated and control groups, respectively, on a given day.

TGI is calculated for each group using the formula. TGI (%)=$[1-(T_i-T_0)/(V_i-V_0)] \times 100$; $T_i$ is the average tumor volume of a treatment group on a given day. $T_0$ is the average tumor volume of the treatment group on the first day of treatment. $V_i$ is the average tumor volume of the vehicle control group on the same day with $T_i$, and $V_0$ is the average tumor volume of the vehicle group on the first day of treatment.

Termination

Bodyweight loss: Any animal exhibiting 20% bodyweight loss at any one day will be humanely killed or the veterinary staff will be contacted Tumor burden: Tumor burden should not exceed 10% of the animal's bodyweight. The study will be terminated with all animals being sacrificed when the mean tumor volume of the vehicle control group reaches a value of 2,000 mm'.

Ulceration

If tumor ulceration occurs. the following procedures will apply.

Animals with ulcerated tumors will be monitored at least 3 times per week with increasing frequency, up to daily, depending upon clinical signs.

Ulcerated tumors, which have not scabbed over, should be cleaned with an appropriate wound cleansing solution (e g. Novalsan). Antibiotic cream is to be applied to the ulceration/lesion only if directed by the Veterinary staff Criteria for euthanasia include if the lesion:

Does not heal or form a scab within 1 week.

Is greater than 5 mm diameter.

Becomes cavitated.

Develops signs of infection (such as presence of pus) or bleeding, or if the animal shows signs of discomfort (e.g. excessive licking and biting directed at the site) or systemic signs of illness (lethargy, decreased activity, decreased food consumption, decreased body condition or weight loss). Contact the veterinary staff to discuss any possible exceptions.

Clinical Signs

Animals must be euthanized if they found to be moribund (unless special permission is granted by the IACUC based on adequate justification. which must be included in the protocol and increased supportive care provided such as warm SC) fluids Diet Gel food cup next to animal so they can reach food, cage on a warming pad for supplemental heat, etc. Note a moribund condition indicates an animal is unlikely to survive.).

Clinical examples of morbidity may include:

Hunched.

Persistent recumbency and lack of response to handling or other stimuli.

Signs of severe organ or system failure.

Emaciation.

Hypothermia.

CNS deficits such as convulsions.

Respiratory: rapid respiratory rate, labored breathing, coughing. Rales.

GE: diarrhea lasting >2 days, jaundice.

Any animal that exhibits the above clinical issues will be humanely sacrificed by $CO_2$.

Necropsy will not be performed in the event of an unexpected death

Statistical Analysis

For comparison between two groups, an independent sample t-test will be used for comparison among three or more groups, a one-way ANOVA will be performed If a significant F-statistics (a ratio of treatment variance to the error variance) is obtained, multiple comparison procedures will be applied after ANOVA. The potential synergistic effect between treatments will be analyzed by two-way ANOVA. All data will be analyzed using SPSS 17.0, p<0.05 is considered to be statistically significant.

FIG. 1 shows the results of the efficacy of BT1718 in the patient-derived xenograft model in female BALB/c nude mice. Dosing at 3 mg/kg biw caused tumor stasis. Dosing at 10 mg/kg biw caused tumor eradication. A lack of relapse is observed after cessation of dosing at 10 mg/kg biw.

Example 4

In Vivo Anti-Tumor Efficacy of BT1718 in the Treatment of MT1-MMP Low-Expressing LU-01-0486 PDX Model in Female BALB/C Nude Mice Study Objective The objective of this study was to evaluate the in vivo anti-tumor efficacy of BT1718 in the treatment of MT1-MMP low-expressing LU-01-0486 PDX model in female Balb/C nude mice Materials: Animal and Housing Conditions Animals Species: *Mus Musculus*

Strain: Balb/C nude

Age: 6-8 weeks

Sex: female

Body weight: 18-22 g

Number of animals: 18 mice plus spare

Housing Conditions

The mice were kept in individual ventilation cages at constant temperature and humidity with 3 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

Experimental Methods and Procedures

Tumor Inoculation

Each mouse was inoculated subcutaneously at the right flank with LU-01-0486 of tumor fragment (30 mm$^3$) for tumor development. The treatments was started when the average tumor volume reaches 164 mm$^3$.

Observations

All the procedures related to animal handling, care and the treatment in the study were performed following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured two times weekly in two dimensions using a caliper, and the volume was expressed in mm$^3$ using the formula: V=0.5 a×b$^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Sample Collection

Mice in group 2, 3 were re-dosed and plasma was collected at 5 min, 15 min, 30 min, 60 min and 120 min on day 24.

The tumor samples were collected and fixed in 10% formalin, then embedded in paraffin and stored at ambient temperature.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. P<0.05 was considered to be statistically significant.

Figure 2:
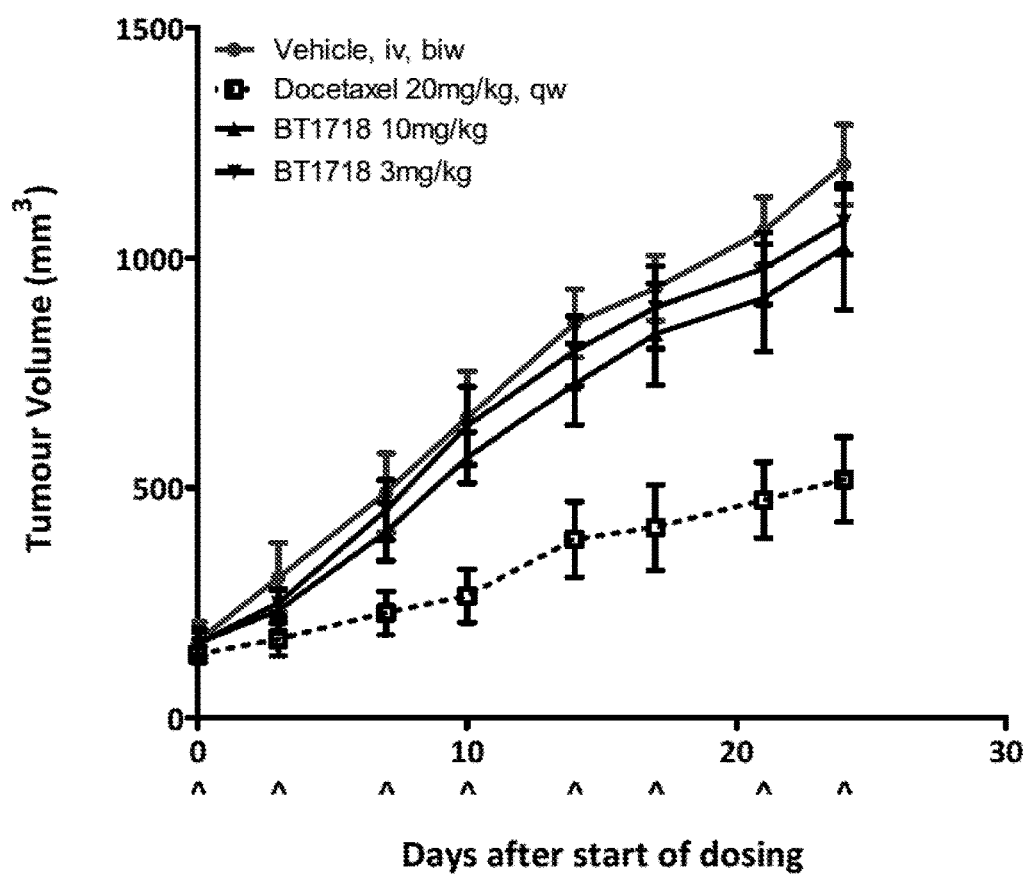
FIG. 2 depicts the efficacy of BT1718 in the MT1-MMP low-expressing LU-01-0486 PDX animal model.

As shown in FIG. 2, the mean tumor size of vehicle-treated animals reached 1201 mm$^3$ on day 24, mice treated with the clinically used agent Docetaxel showed significant inhibition of tumor growth, but with severe weight loss, leading to the humane sacrifice of animals at day 24. Mice dosed with BT1718 at 3 or 10 mg/kg showed limited inhibition of tumor growth and no significant effect on body weight.

Example 5

Evaluation of the Efficacy of BT1718 in a Patient-Derived Xenograft (PDX) Model in Female BALB/C Nude Mice Study Objective The objective of the project is to evaluate the in vivo therapeutic efficacy of test articles in the LU-01-0251 non-small-cell lung carcinoma (NSCLC) PDX model. LU-01-0251 is a high MT1-expressing NSCLC that is docetaxel sensitive.

Study Design

The NSCLC PDX model will be used in this study as shown in Table 41.

TABLE 41

NSCLC PDX model used in study

| Model Name | Cancer Type | Tumor growth speed | Array | RSQ | MT1-MMP expression |
|---|---|---|---|---|---|
| LU-01-0251 | NSCLC | Tumor size can reach 1000 mm$^3$ in 40 days after tumor inoculation | 9.88 | 367.003 | High |

Animals

Balb/C nude, female, 6-8 weeks, weighing approximately 18-22 g.

Tumor Inoculation

Each mouse was inoculated subcutaneously at the right flank with certain kind of tumor fragment (30 mm3) for tumor development. The treatments started when the average tumor volume reaches approximately 150-200 mm$^3$. The test article administration and the animal numbers in each group are shown in Table 40 which details the experimental design.

TABLE 42

Study Design

| Group | Treatment | n | Dose (mg/kg) | Dosing Volume (μL/g) | Dosing Route | Schedule |
|---|---|---|---|---|---|---|
| 1 | Vehicle | 6 | — | 10 | iv | biw × 4 wks |
| 2 | BT1718 | 6 | 3 | 10 | iv | biw × 4 wks |
| 3 | BT1718 | 6 | 10 | 10 | iv | biw × 4 wks |
| 4 | Docetaxel | 6 | 20 | 10 | iv | biw × 4 wks |

Treatment was given until the control tumors reached an average of 1000 mm$^3$.

Animal Housing

An acclimation period of approximately one week will be allowed between animal arrival and tumor inoculation in order to accustom the animals to the laboratory environment. The mice will be maintained in a special pathogen-free environment and in individual ventilation cages (3 mice per cage). All cages, bedding, and water will be sterilized before use when working in the mouse room, the investigators will wear lab coat and latex or vinyl gloves. Each cage will be clearly labeled with a cage card indicating number of animals, sex, strain, date received, treatment, study number, group number and the starting date of the treatment The cages with food and water will be changed twice a week. The targeted conditions for animal room environment and photoperiod will be as follows:

Temperature: 20-26° C.
Humidity: 40-70%
Light cycle: 12 hours light and 12 hours dark Dietary Materials All animals will have free access to a standard certified commercial laboratory diet. Maximum allowable concentrations of contaminants in the diet are controlled and routinely analyzed by the manufacturers. Autoclaved municipal tap water suitable for human consumption will be available to the animals ad libitum. It is considered that there are no known contaminants in the dietary materials that could influence the tumor growth Assignment to Groups Before commencement of treatment all animals will be weighed and the tumor volumes will be measured. Since the tumor volume can affect the effectiveness of any given treatment, mice will be assigned into groups using randomized block design based upon their tumor volumes. This ensures that all the groups are comparable at the baseline.

Observations

The protocol and any amendment(s) or procedures involving the care and use of animals in this study will be reviewed and approved prior to conduct. During the study, the care and use of animals will be conducted in accordance with the regulations of the Association for Assessment and Accreditation of Laboratory Animal Care (AAALAC). After inoculation, the animals will be checked daily for morbidity and mortality. At the time of routine monitoring, the animals will be checked for any effects of tumor growth and treatments on normal behavior such as mobility, food and water consumption, body weight gain/loss (body weights will be measured twice weekly), eye/hair matting and any other abnormal effect. Death and observed clinical signs will be recorded on the basis of the numbers of animals within each subset.

Endpoints

The major endpoint is to see if the tumor growth can be delayed or mice can be cured. Tumor sizes will be measured twice weekly in two dimensions using a caliper and the volume will be expressed in mm$^3$ using the formula: V=0.5 a×b$^2$ where a and b are the long and short diameters of the tumor, respectively. The tumor sizes are then used for the calculations of both T-C and TIC values. T-C is calculated with T as the median time (in days) required for the treatment group tumors to reach a predetermined size (e.g., 1.000 mm$^3$), and C is the median time (in days) for the control group tumors to reach the same size. The TIC value (in percent) is an indication of antitumor effectiveness, T and C are the mean volume of the treated and control groups, respectively, on a given day.

TGI is calculated for each group using the formula. TGI (%)=[1−(Ti−T0)/(Vi-V0)]×100; Ti is the average tumor volume of a treatment group on a given day. T0 is the average tumor volume of the treatment group on the first day of treatment. Vi is the average tumor volume of the vehicle control group on the same day with Ti, and V0 is the average tumor volume of the vehicle group on the first day of treatment.

Termination

Bodyweight loss: Any animal exhibiting 20% bodyweight loss at any one day will be humanely killed or the veterinary staff will be contacted Tumor burden: Tumor burden should not exceed 10% of the animal's bodyweight. The study will be terminated with all animals being sacrificed when the mean tumor volume of the vehicle control group reaches a value of 2,000 mm'.

Ulceration

If tumor ulceration occurs. the following procedures will apply.

Animals with ulcerated tumors will be monitored at least 3 times per week with increasing frequency, up to daily, depending upon clinical signs.

Ulcerated tumors, which have not scabbed over, should be cleaned with an appropriate wound cleansing solution (e g. Novalsan). Antibiotic cream is to be applied to the ulceration/lesion only if directed by the Veterinary staff Criteria for euthanasia include if the lesion:

Does not heal or form a scab within 1 week.

Is greater than 5 mm diameter.

Becomes cavitated.

Develops signs of infection (such as presence of pus) or bleeding, or if the animal shows signs of discomfort (e.g. excessive licking and biting directed at the site) or systemic signs of illness (lethargy, decreased activity, decreased food consumption. decreased body condition or weight loss). Contact the veterinary staff to discuss any possible exceptions.

Clinical Signs

Animals must be euthanized if they found to be moribund (unless special permission is granted by the IACUC based on adequate justification. which must be included in the protocol and increased supportive care provided such as warm SO fluids Diet Gel food cup next to animal so they can reach food, cage on a warming pad for supplemental heat, etc. Note a moribund condition indicates an animal is unlikely to survive.).

Clinical examples of morbidity may include:

Hunched.

Persistent recumbency and lack of response to handling or other stimuli.

Signs of severe organ or system failure.

Emaciation.

Hypothermia.

CNS deficits such as convulsions.

Respiratory: rapid respiratory rate, labored breathing, coughing. Rales.

GI: diarrhea lasting >2 days, jaundice.

Any animal that exhibits the above clinical issues will be humanely sacrificed by $CO_2$.

Necropsy will not be performed in the event of an unexpected death

Statistical Analysis

For comparison between two groups, an independent sample t-test will be used for comparison among three or more groups, a one-way ANOVA will be performed If a significant F-statistics (a ratio of treatment variance to the error variance) is obtained, multiple comparison procedures will be applied after ANOVA. The potential synergistic effect between treatments will be analyzed by two-way ANOVA. All data will be analyzed using SPSS 17.0, p<0.05 is considered to be statistically significant.

Figure 3:
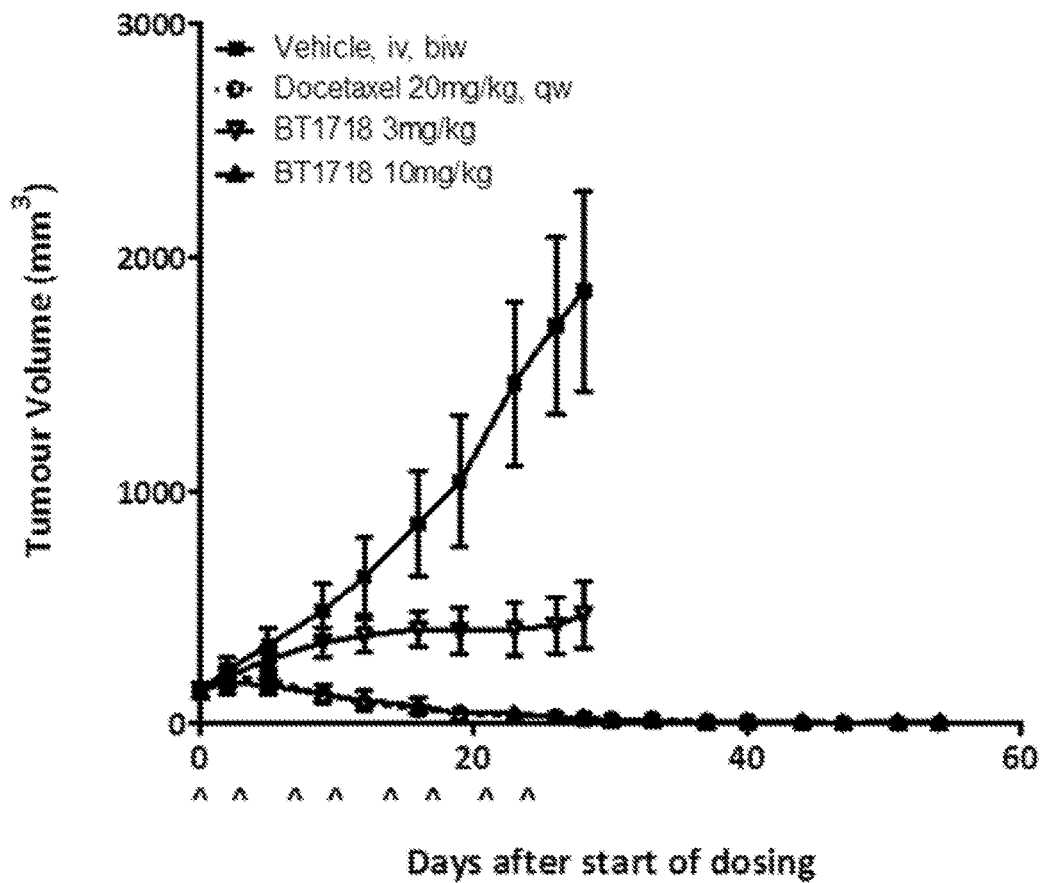
FIG. 3 depicts the efficacy of BT1718 in the MT1-MMP high expressing docetaxel sensitive non-small-cell lung carcinoma (NSCLC) patient-derived xenograft (PDX) animal model.

FIG. 3 shows the results of the efficacy of BT1718 in the patient-derived xenograft model in female BALB/c nude mice. Dosing at 3 mg/kg biw caused tumor stasis. Dosing at 10 mg/kg biw caused tumor eradication. A lack of relapse is observed after cessation of dosing at 10 mg/kg biw.

Figure 4:
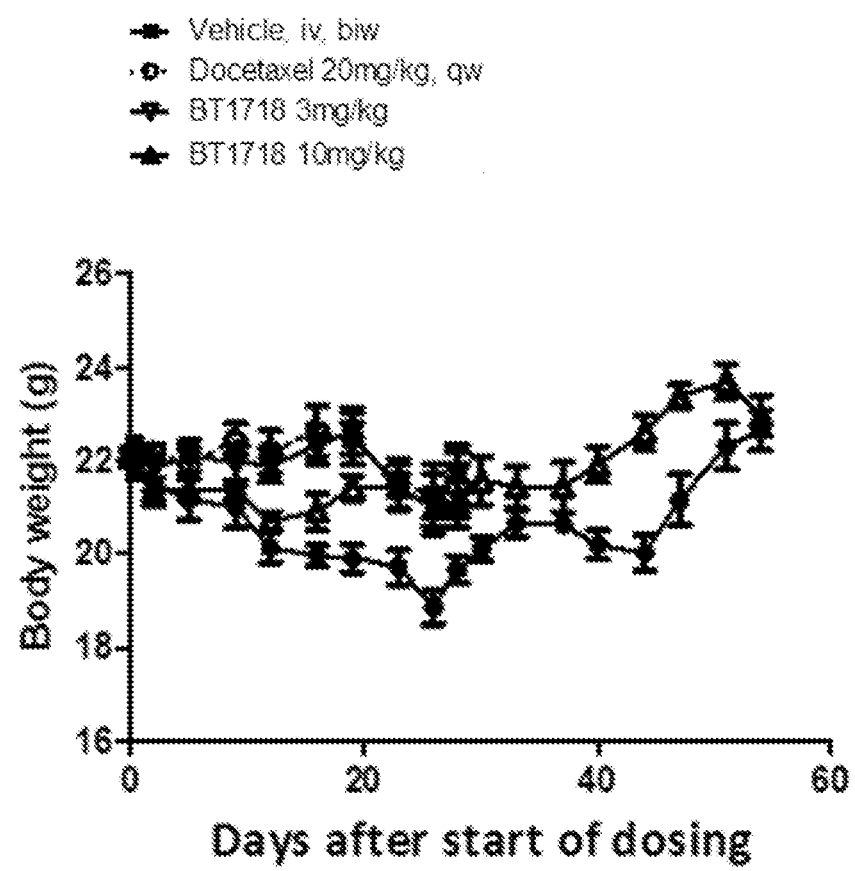
FIG. 4 depicts the body weight changes observed during the efficacy study of BT1718 in the MT1-MMP high expressing docetaxel sensitive non-small-cell lung carcinoma (NSCLC) patient-derived xenograft (PDX) animal model.

FIG. 4 depicts the body weight changes observed during the efficacy study of BT1718 in the MT1-MMP high expressing docetaxel sensitive non-small-cell lung carcinoma (NSCLC) patient-derived xenograft (PDX) animal model.

Example 6

Evaluation of the Efficacy of BT1721 in EBC-1 Xenograft Model in Female BALB/C Nude Mice Study Objective The objective of this study was to evaluate the anti-tumor efficacy of BT1721 in EBC-1 xenograft model in female BALB/c nude mice.

TABLE 43

Experimental Design

| Gr | n | Treatment | Dose (mg/kg) | Dose volume(ml/kg) | Conc. (mg/ml) | Dosing Route | Schedule |
|----|---|-----------|--------------|--------------------|--------------|--------------|----------|
| 1 | 3 | BT1721 | 1 | 10 | 0.1 | IV | 3x weekly for 2 weeks (D 0, 2, 4, 7, 9, 11, 14) |

TABLE 43-continued

Experimental Design

| Gr | n | Treatment | Dose (mg/kg) | Dose volume(ml/kg) | Conc. (mg/ml) | Dosing Route | Schedule |
|---|---|---|---|---|---|---|---|
| 2 | 3 | BT1721 | 3 | 10 | 0.3 | IV | 3x weekly for 2 weeks (D 0, 2, 4, 7, 9, 11, 14) |
| 3 | 3 | BT1721 | 10 | 10 | 1 | IV | 3x weekly for 2 weeks (D 0, 2, 4, 7, 9, 11, 14) |

Note:
n: animal number; Dosing volume: adjust dosing volume based on body weight 10 μl/g.

Materials
Animals and Housing Condition
  Animals
    Species: *Mus Musculus*
    Strain: Balb/c nude
    Age: 6-8 weeks
    Sex: female
    Body weight: 18-22 g
    Number of animals: 9 mice plus spare
    Animal supplier: Shanghai SLAC Laboratory Animal Co., LTD.
Housing Condition
  The mice were kept in individual ventilation cages at constant temperature and humidity with 3 animals in each cage.
    Temperature: 20~26° C.
    Humidity 40-70%.
    Cages: Made of polycarbonate. The size is 300 mm×180 mm×150 mm. The bedding material is corn cob, which is changed twice per week.
    Diet: Animals had free access to irradiation sterilized dry granule food during the entire study period.
    Water: Animals had free access to sterile drinking water.
    Cage identification: The identification labels for each cage contained the following information: number of animals, sex, strain, date received, treatment, study number, group number and the starting date of the treatment.
    Animal identification: Animals were marked by ear coding.
Test and Positive Control Articles
  Product identification: BT1721
  Manufacturer: Bicycle Therapeutics
  Lot number: N/A
  Physical description: Clear solution (in DMSO)
  Molecular weight: 3772.65, Formula weight: 3772.65, Purity: >95%
  Package and storage condition: stored at −80° C.
Experimental Methods and Procedures
Cell Culture
  The EBC-1 tumor cells were maintained in vitro as a monolayer culture in RPMI1640 medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.
Tumor Inoculation
  Each mouse was inoculated subcutaneously at the right flank with EBC-1 tumor cells ($10 \times 10^6$) in 0.2 ml of PBS for tumor development. The treatments were started on Day 7 after the tumor inoculation when the average tumor size reached approximately 152 $mm^3$. Each group consisted of 3 tumor-bearing mice. The testing articles were administrated to the mice according to the predetermined regimen as shown in the experimental design (Table 43).
Observations
  All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.
Tumor Measurements and the Endpoints
  The major endpoint was to see if the tumor growth could be delayed or mice could be cured. Tumor size was measured three times weekly in two dimensions using a caliper, and the volume was expressed in $mm^3$ using the formula: $V=0.5 \ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.
  TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.
Statistical Analysis
  Summary statistics, including mean and the standard error of the mean (SEM), are provided for the tumor volume of each group at each time point.
  Statistical analysis of difference in tumor volume among the groups was conducted on the data obtained at the best therapeutic time point after the final dose.
  A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant.
Results
Mortality, Morbidity, and Body Weight Gain or Loss
  Animal body weight was monitored regularly as an indirect measure of toxicity. Body weight change in female BALB/c nude mice bearing EBC-1 dosed with BT1721 is shown in Tables 44 and 45. Mice treated with BT1721 maintained their bodyweight well.

TABLE 44

Body Weight (g)

| Group | Days after the start of treatment | | | | | | |
|---|---|---|---|---|---|---|---|
| | 0 | 2 | 4 | 7 | 9 | 11 | 14 |
| Vehicle, tiw | 22.0 ± 0.2 | 22.0 ± 0.3 | 22.7 ± 0.1 | 22.9 ± 0.2 | 23.9 ± 0.1 | 23.7 ± 0.1 | 23.9 ± 0.0 |
| BT1721, 1 mpk, tiw | 22.2 ± 0.7 | 22.0 ± 0.5 | 22.4 ± 0.8 | 22.5 ± 0.9 | 23.2 ± 0.8 | 22.9 ± 1.0 | 23.3 ± 1.1 |
| BT1721, 3 mpk, tiw | 22.9 ± 0.4 | 22.3 ± 0.6 | 22.3 ± 0.8 | 23.1 ± 0.7 | 23.9 ± 1.0 | 24.0 ± 1.0 | 24.6 ± 1.0 |
| BT1721, 10 mpk, tiw | 23.2 ± 0.5 | 23.2 ± 0.3 | 23.2 ± 0.4 | 23.9 ± 0.5 | 24.4 ± 0.4 | 24.4 ± 0.6 | 25.3 ± 0.5 |

TABLE 45

Body Weight (% Change)

| Group | Days after the start of treatment | | | | | | |
|---|---|---|---|---|---|---|---|
| | 0 | 2 | 4 | 7 | 9 | 11 | 14 |
| Vehicle, tiw | 0.0 | 0.1 ± 1.3 | 3.3 ± 0.9 | 4.4 ± 0.3 | 8.9 ± 1.2 | 7.8 ± 0.8 | 8.9 ± 1.4 |
| BT1721, 1 mpk, tiw | 0.0 | −1.1 ± 0.7 | 0.8 ± 2.3 | 1.3 ± 1.4 | 4.4 ± 0.8 | 3.1 ± 1.7 | 4.6 ± 2.0 |
| BT1721, 3 mpk, tiw | 0.0 | −2.8 ± 1.3 | −2.8 ± 1.9 | 0.8 ± 1.8 | 4.0 ± 2.8 | 4.7 ± 2.7 | 7.2 ± 2.9 |
| BT1721, 10 mpk, tiw | 0.0 | 0.0 ± 1.5 | −0.3 ± 0.5 | 2.8 ± 0.6 | 5.1 ± 0.6 | 5.0 ± 0.3 | 8.8 ± 0.7 |

Tumor Volume Trace

Mean tumor volume over time in female Balb/c nude mice bearing EBC-1 xenograft is Shown in Table 46

TABLE 46

The tumor volume trace over time

| Group | Days after the start of treatment | | | | | | |
|---|---|---|---|---|---|---|---|
| | 0 | 2 | 4 | 7 | 9 | 11 | 14 |
| Vehicle tiw | 146 ± 24 | 309 ± 3 | 443 ± 18 | 730 ± 56 | 925 ± 35 | 1061 ± 118 | 1195 ± 91 |
| BT1721, 1 mg/kg, tiw | 164 ± 31 | 291 ± 57 | 367 ± 68 | 640 ± 39 | 784 ± 40 | 874 ± 50 | 981 ± 47 |
| BT1721, 3 mg/kg, tiw | 142 ± 18 | 207 ± 60 | 310 ± 61 | 531 ± 116 | 708 ± 132 | 761 ± 147 | 920 ± 210 |
| BT1721, 10 mg/kg, tiw | 160 ± 25 | 249 ± 82 | 407 ± 85 | 632 ± 149 | 735 ± 201 | 858 ± 72 | 1142 ± 147 |

Tumor Growth Inhibition Analysis

Tumor growth inhibition rate for BT1721 in the EBC-1 xenograft model was calculated based on tumor volume measurements at day 14 after the start of treatment. The results are displayed in Table 6.

TABLE 47

Tumor growth inhibition analysis (T/C and TGI)

| Gr | Treatment | Tumor Size (mm$^3$)$^a$ | T/C$^b$ (%) | TGI (%) | P value |
|---|---|---|---|---|---|
| 1 | Vehicle, tiw | 1195 ± 91 | — | — | — |
| 2 | BT1721, 1 mg/kg, tiw | 981 ± 47 | 22 | 82 | ns |
| 3 | BT1721, 3 mg/kg, tiw | 920 ± 210 | 26 | 77 | ns |
| 4 | BT1721 10 mg/kg, tiw | 1142 ± 147 | 6 | 96 | ns |

$^a$Mean ± SEM.

$^b$Tumor Growth Inhibition is calculated by dividing the group average tumor volume for the treated group by the group average tumor volume for the control group (T/C). For a test article to be considered to have anti-tumor activity, T/C must be 50% or less. Dunnett's One-way ANOVA was conducted to analysis the statistical differences of compound-treatment groups vs Vehicle group on day 14, ns indicates non-significant.

45

Results Summary and Discussion

In this study, the therapeutic efficacy of BT1721 in the EBC-1 xenograft model was evaluated. The measured body weight and body weight changes are shown in the Tables 44 and 45. Tumor sizes of all treatment groups at various time points are shown in Tables 46 and 47.

The mean tumor size of vehicle treated mice reached 1195 mm³ on day 14, mice treated with BT1721 at the 1 mg/kg, 3 mg/kg and 10 mg/kg didn't show any inhibitory effect on tumor growth.

Example 7

Synthesis of BT1721

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-tris(bromomethyl) benzene (TBMB, Sigma). For this, linear peptide was diluted with H₂O up to ~35 mL, ~500 µL of 100 mM TBMB in acetonitrile was added, and the reaction was initiated with 5 mL of 1 M NH4HCO3 in H2O. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

The structure of the Bicycle 17-69-07-N260 used to prepare BT1721 is shown below:

46

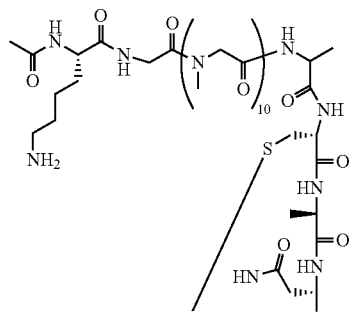

17-69-07-N260

Preparation of BT1721

Reaction Scheme:

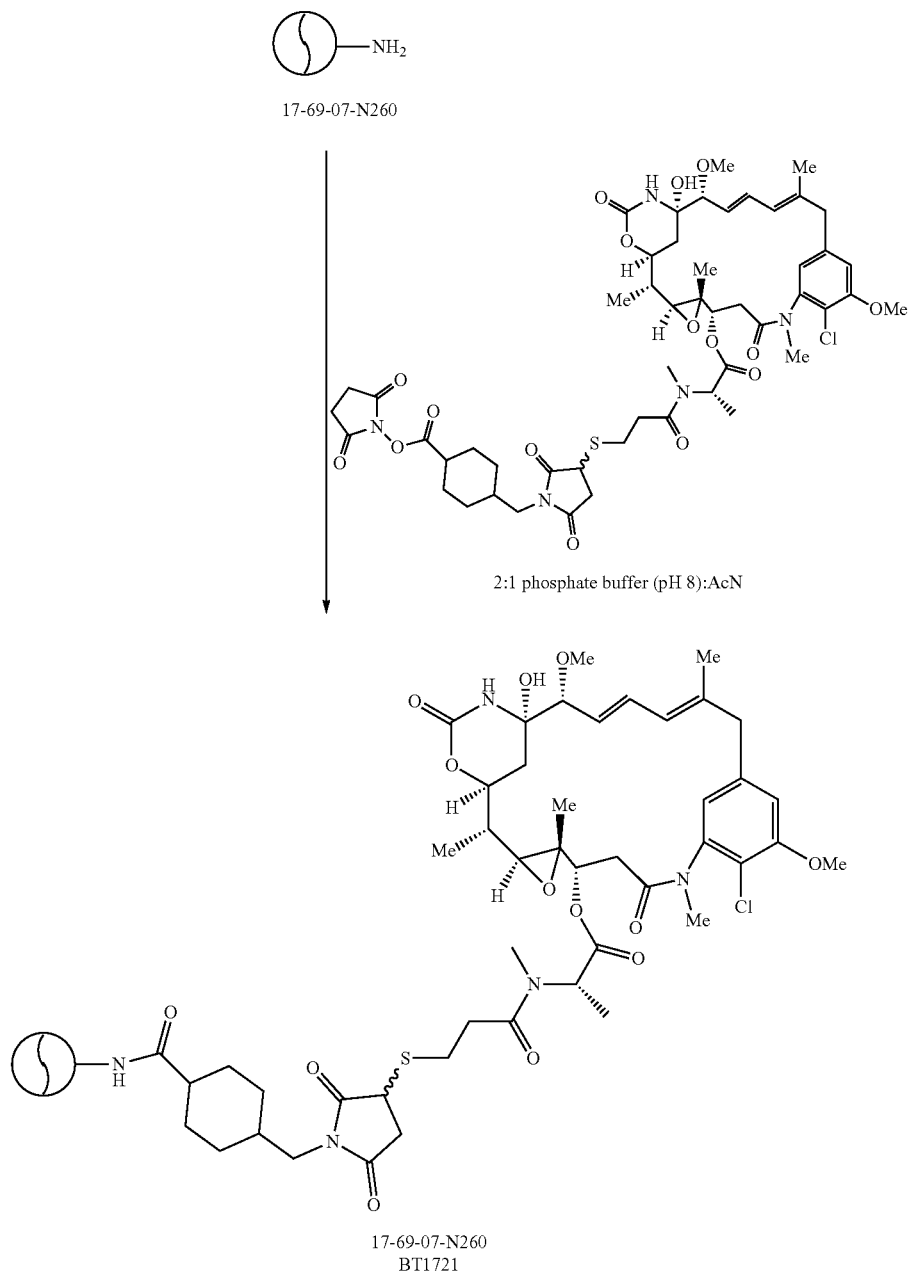

In a 50 mL conical tube, containing a stirbar, a 5 mg/mL solution of peptide 17-69-07-N260 (30 mg) was prepared using 6.0 mL sodium phosphate buffer (100 mM, pH 8.0). To this stirring solution was first added AcN (3.0 mL), followed by the addition of the NETS-ester derivative of the payload* (315 μL, 50 mM in DMSO) was added via pipetman. The resultant solution was stirred at room temperature. The reaction progress was monitored by LC/MS and was deemed complete after 2.5 hrs. The desired product was obtained via direct purification of the reaction mixture using a 50 g RediSep® Rf reversed phase C18 column and a solvent gradient of 0% B to 75% B over 20 minutes. Material obtained was not deemed pure enough for submission and so the conjugation was performed a second time (27 mg scale, peptide). The combined crude material from the two conjugations was purified using a 50 g RediSep® Rf reversed phase C18 column and a solvent gradient of 0% B to 95% B over 45 minutes. Pure fractions were combined and lyophilized to give 11.1 mg (15% yield) of the desired product as a fluffy white solid. Analysis by LC/MS indicated the material was at >95% purity (retention time: 3.00 min).

LC/MS (ES+) calc for [M-$H_2O$+3]+/3 1252; found 1252.
* Obtained from commercial sources
The structure of BT1721 is shown below.

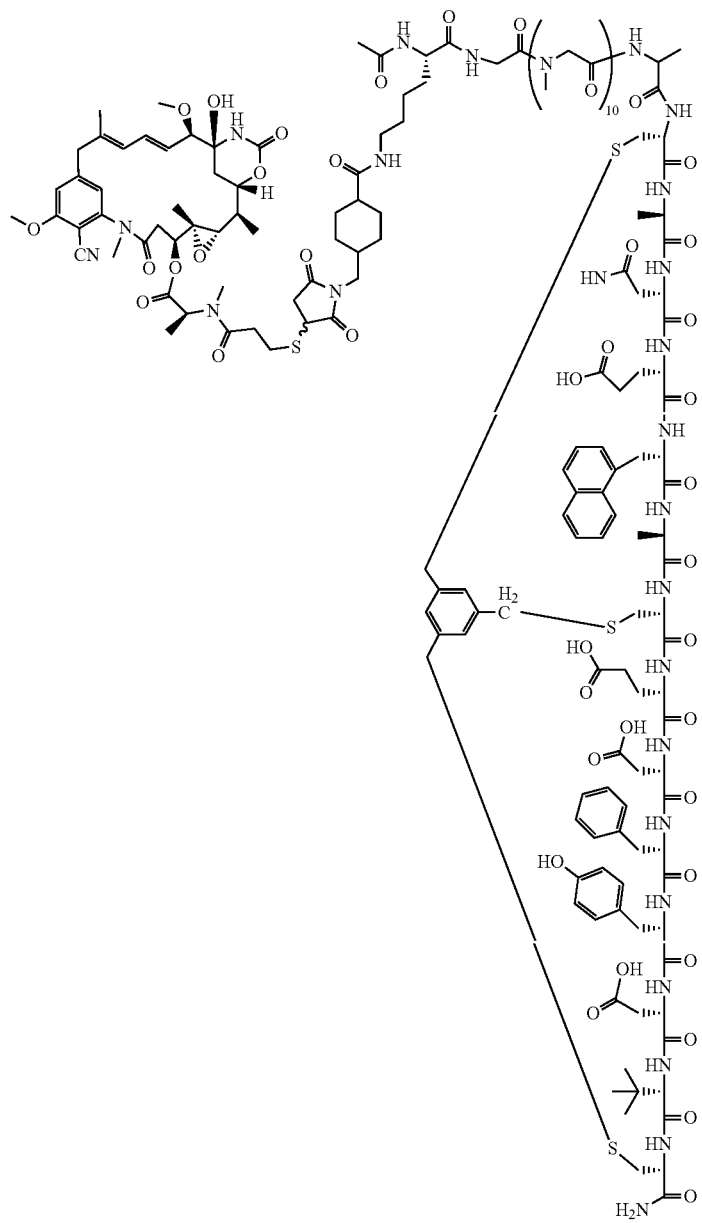

BT1721

Example 8

In Vitro Cytotoxicity Testing of BT1718 and BT1721 in an HT1080 Cell Line

Study Objective

To evaluate the in vitro cytotoxicity of BT1718 and BT1721 in an HT1080 cell line using an ATP endpoint assay after 72 hours incubation.

Methods

Cells were seeded in 96 well plates (75 µl/well, HT1080=7500–15000 cell/well) and incubated overnight at 37° C.+5% $CO_2$.

The day after cell seeding, serial dilutions (1:5) of BT1718 and BT1721 were prepared in DMSO and diluted 1:71 in cell culture media to give 4× final concentrations. Twenty five µl/well was added to the cells (2 µM or 5 µM top final concentration of BT1718 and 2 µM or 5 µM top final concentration of BT1721, <0.6% final DMSO).

Cells were 30-50% confluent upon dosing. Control wells containing 5 µM final concentration of staurosporine (positive control), lysis buffer (1% NP40, 20 mM Tris pH8, 137 mM NaCl, 10% glycerol, 2 mM EDTA, 1 mM Na Orthovanadate, 10 µg/ml leupeptin, 10 µg/ml aprotinin) positive control or media (negative control), were also included. Plates were sealed with gas permeable seals and incubated at 37° C.+5% $CO_2$ for 72 hours. No wash steps were performed.

After a total of 72 hours after dosing, ATPLite reagent (Perkin Elmer) was equilibrated to room temperate and reconstituted in the supplied buffer as per the manufacturer's instructions. One hundred μl 1× detection reagent was added per well. Plates were sealed, protected from light and shaken gently for 20 minutes to ensure complete cell lysis before luminescence was read using a BMG Pherastar FS plate reader. Luminescence counts directly correlate with ATP levels and hence cell viability. Data was analysed using GraphPad Prism. Non-linear regression fit was used to calculate a relative $IC_{50}$ for each toxic agent: Y=Bottom+ (Top−Bottom)/(1+10^((Log Ic50−X)*HillSlope)) where the $IC_{50}$ is defined as 50% of the total cell kill achieved at the top concentration of toxin.

Results

BT1718 $IC_{50}$=1.0 nM.
BT1721 $IC_{50}$=8.9 nM.

Example 9

In Vivo Efficacy Test of BT1718 in the Treatment of 3LL Syngeneic Model in C57BL/6 Mice Study Objective The objective of this study was to evaluate the in vivo anti-tumor efficacy of BT1718 in the treatment of the subcutaneous 3LL syngeneic model in C57BL/6 mice.

Study Design

The study design is shown in Table 48, below.

TABLE 48

Experimental design

| Group | BDCs | Dosage (mg/kg) | n | Dosing volume(ml/kg) | route | Schedule |
|---|---|---|---|---|---|---|
| 1 | Vehicle | — | 6 | 10 | i.v. | biw*2 weeks |
| 2 | BT1718 | 1 | 6 | 10 | i.v. | biw*2 weeks |
| 3 | BT1718 | 3 | 6 | 10 | i.v. | biw*2 weeks |
| 4 | BT1718 | 10 | 6 | 10 | i.v. | biw*2 weeks |

Animals
  Species: *Mus Musculus*
  Strain: C57BL/6 mice
  Age: 6-10 weeks
  Sex: Female
  Body weight: 18-22 g
  Number of animals: 24 plus spare Housing Condition The animals were kept in ventilation cages at constant temperature and humidity with 3 animals in each cage.
  Temperature: 20-26° C.
  Humidity: 40-70%.
  Cages: Made of polycarbonate. The size is 300 mm×180 mm×150 mm. The bedding material is corn cob, which was changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.

Test and Positive Control Articles
  Product identification: BT1718

Manufacturer: Bicycle Therapeutics
  Lot number: N/A
  Physical description: Lyophilized powder
  Molecular weight: 3511.4
  Package and storage condition: stored at −80° C.

Cell Culture

The 3LL tumor cells were maintained in vitro as a monolayer culture in medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Tumor Inoculation

Each mouse was inoculated subcutaneously at the right flank with 3LL tumor cells (1×106) in 0.1 ml of PBS for tumor development. The animals were randomized and treatment was started when the average tumor volume reaches approximately 105 $mm^3$ for the efficacy study. The test article administration and the animal numbers in each group were shown in the experimental design table (Table 48).

Testing Article Formulation Preparation

The formulation of the testing article is shown in Table 49, below.

TABLE 49

Testing Article Formulation Preparation

| Test article | Con. (mg/ml) | Formulation | Buffer |
|---|---|---|---|
| Vehicle | — | 25 mM Histidine pH 7, 10% Sucrose | — |
| BT1718 | 1.0 | Add 10 mg BT1718 into 10 ml buffer, sonicate and shake to ensure the solution to be clear | 25 mM Histidine pH 7, 10% Sucrose |
| | 0.3 | Add 240 ul 1.0 mg/ml BT1718 into 560 ul buffer, shake to ensure the solution to be clear | |
| | 0.1 | Add 80 ul 1.0 mg/ml BT1718 into 720 ul buffer, shake to ensure the solution to be clear | |

Observations

All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured three times weekly in two dimensions using a caliper, and the volume was expressed in $mm^3$ using the formula: V=0.5 a×b2 where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. P<0.05 was considered to be statistically significant.

Results

Body Weight Curve

Figure 5:
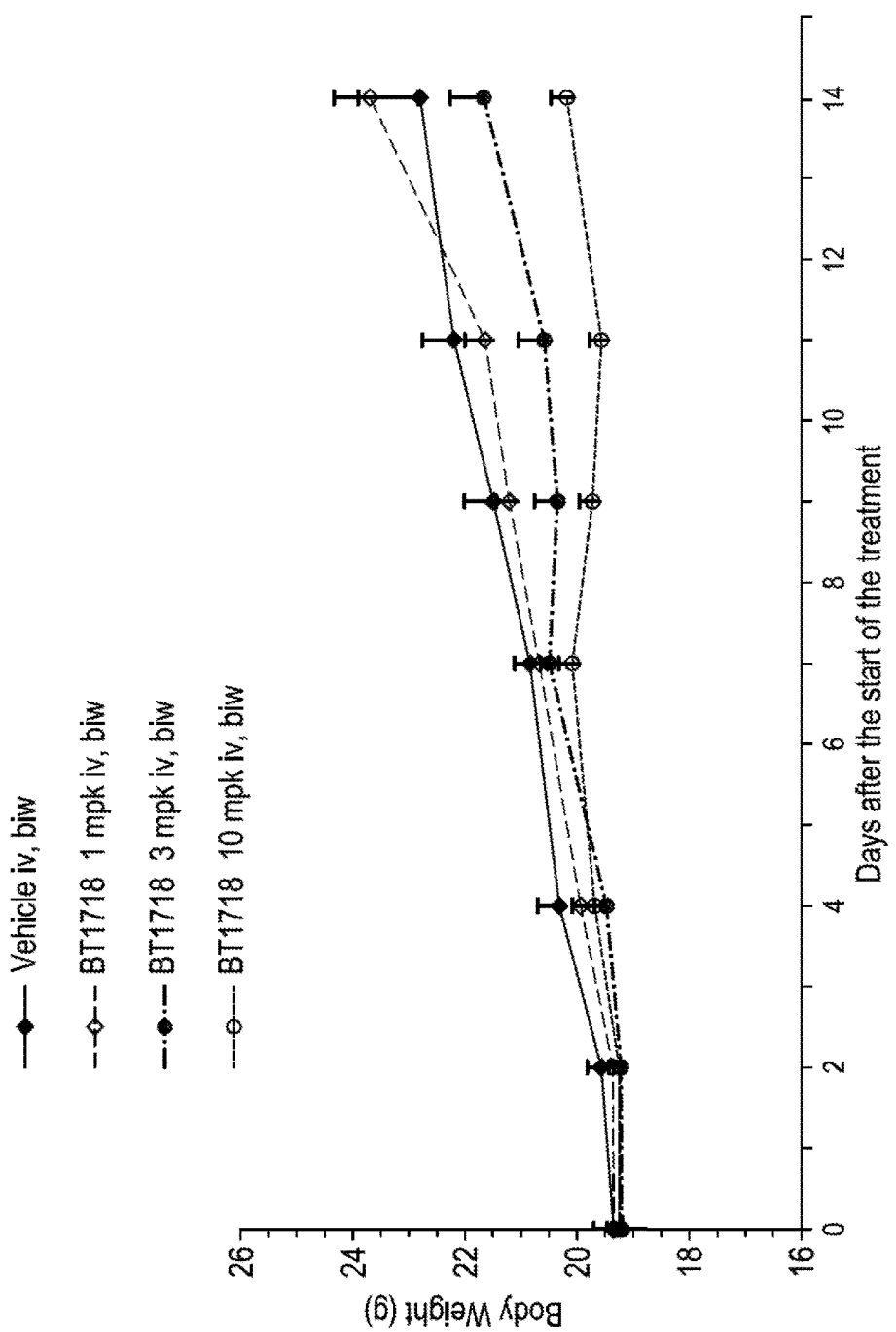
FIG. 5 depicts body weight changes after the treatment of BT1718 to C57BL/6 mice bearing 3LL tumor. Data points represent group mean body weight. Error bars represent standard error of the mean (SEM).

The body weight changes after the treatment of BT1718 to C57BL/6 mice bearing 3LL tumor are shown in FIG. 5. Data points represent group mean body weight. Error bars represent standard error of the mean (SEM).

Tumor Volume Trace

Mean tumor volume over time in female C57BL/6 mice bearing 3LL tumor is shown in Table 50.

TABLE 51

Tumor growth inhibition analysis (T/C and TGI)

| Gr | Treatment | Tumor Volume (mm$^3$)[a] | T/C[b] (%) | TGI (%) | P value |
|---|---|---|---|---|---|
| 1 | Vehicle, biw | 2524 ± 676 | — | — | — |
| 2 | BT1718, 1 mpk, biw | 2649 ± 553 | 104.9 | −5.1 | p > 0.05 |
| 3 | BT1718, 3 mpk, biw | 1764 ± 471 | 69.9 | 31.4 | p > 0.05 |
| 4 | BT1718, 10 mpk, biw | 350 ± 105 | 13.8 | 89.9 | p < 0.05 |

[a]Mean ± SEM.
[b]Tumor Growth Inhibition is calculated by dividing the group average tumor volume for the treated group by the group average tumor volume for the control group (T/C).

Summary and Discussion

In this study, the in vivo anti-tumor efficacy of BT1718 in the 3LL syngeneic model in C57BL/6 mice was evaluated. The measured body weights are shown in the FIG. 5. Tumor volume of all treatment groups at various time points are shown in Tables 50 and 51 and FIG. 6.

The mean tumor volume of vehicle treated mice reached 2524 mm$^3$ on day 14 after the start of treatment. BT1718 at 1 mg/kg, 3 mg/kg and 10 mg/kg showed dose-dependent antitumor activity with tumor measured at 2649 mm$^3$ (TGI=104.9%, p>0.05), 1764 mm$^3$ (TGI=69.9%, p>0.05) and 350 mm$^3$ (TGI=89.9, p<0.05) respectively. In this study, all mice maintained their bodyweight well.

TABLE 50

Tumor Volume Trace Over Time

| | | Days after the start of treatment | | | | | |
|---|---|---|---|---|---|---|---|
| Gr. Treatment | 0 | 2 | 4 | 7 | 9 | 11 | 14 |
| 1 Vehicle, biw | 105 ± 8 | 232 ± 43 | 400 ± 97 | 735 ± 206 | 1060 ± 329 | 1572 ± 430 | 2524 ± 676 |
| 2 BT1718, 1 mpk, biw | 106 ± 10 | 239 ± 47 | 405 ± 98 | 765 ± 190 | 1120 ± 267 | 1568 ± 392 | 2649 ± 553 |
| 3 BT1718, 3 mpk, biw | 105 ± 9 | 234 ± 48 | 423 ± 86 | 706 ± 152 | 991 ± 245 | 1149 ± 313 | 1764 ± 471 |
| 4 BT1718, 10 mpk, biw | 106 ± 8 | 181 ± 21 | 272 ± 38 | 339 ± 86 | 321 ± 85 | 343 ± 92 | 350 ± 105 |

Tumor Growth Curve

Figure 6:
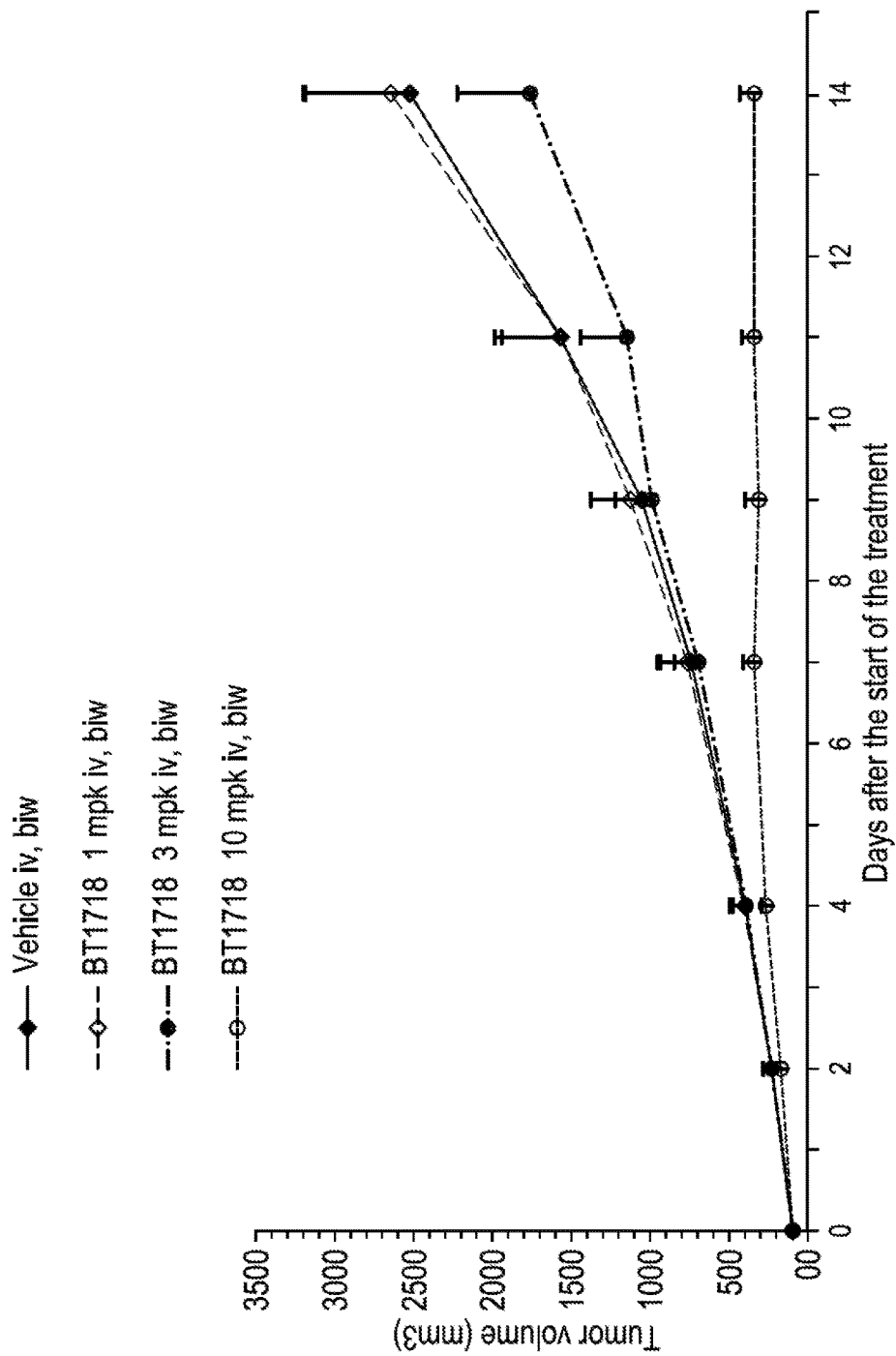
FIG. 6 depicts the tumor volume trace after administering BT1718 to female C57BL/6 mice bearing 3LL tumor. Data points represent group mean, error bars represent standard error of the mean (SEM).

The tumor growth curve is shown in FIG. 6.

FIG. 6 displays the tumor volume trace after administering BT1718 to female C57BL/6 mice bearing 3LL tumor. Data points represent group mean, error bars represent standard error of the mean (SEM).

Tumor Growth Inhibition Analysis

Tumor growth inhibition rate for BT1718 in the 3LL syngeneic model was calculated based on tumor volume measurements at day 14 after the start of treatment.

Example 10

In Vivo Efficacy Test of BT1718 Alone or in Combination with Anti-PD-1 Antibody in the Treatment of 3LL Syngeneic Model in C57BL/6 Mice Study Objective The objective of the research was to evaluate the in vivo anti-tumor efficacy of BT1718 alone or in combination with Anti-PD-1 antibody in the treatment of the subcutaneous 3LL syngeneic model in C57BL/6 mice.

Experimental Design

TABLE 52

Experimental design

| Gr | n | I/O | Dose(mg/kg) | frequency | compound | Dose(mg/kg) | frequency |
|---|---|---|---|---|---|---|---|
| 1 | 6 | Vehicle | — | biw*2 weeks | Vehicle | — | biw*2 weeks |
| 2 | 6 | Vehicle | — | biw*2 weeks | BT1718 | 3 | biw*2 weeks |
| 3 | 6 | Vehicle | — | biw*2 weeks | BT1718 | 10 | biw*2 weeks |
| 4 | 6 | aPD-1 | 10 | biw*2 weeks | Vehicle | — | biw*2 weeks |
| 5 | 6 | aPD-1 | 10 | biw*2 weeks | BT1718 | 3 | biw*2 weeks |
| 6 | 6 | aPD-1 | 10 | biw*2 weeks | BT1718 | 10 | biw*2 weeks |

Materials
Animals
 Species: *Mus Musculus*
 Strain: C57BL/6 mice
 Age: 6-10 weeks
 Sex: Female
 Body weight: 18-22 g
 Number of animals: 36 plus spare
Housing Condition
 The animals were kept in ventilation cages at constant temperature and humidity with 3 animals in each cage.
 Temperature: 20~26° C.
 Humidity: 40-70%.
 Cages: Made of polycarbonate. The size is 300 mm×180 mm×150 mm. The bedding material is corn cob, which was changed twice per week.
 Diet: Animals had free access to irradiation sterilized dry granule food during the entire study period.
 Water: Animals had free access to sterile drinking water.
 Cage identification: The identification labels for each cage contained the following information: number of animals, sex, strain, the date received, treatment, study number, group number and the starting date of the treatment.
 Animal identification: Animals were marked by ear coding.
Test and Positive Control Articles
 Product identification: BT1718
 Manufacturer: Bicycle Therapeutics
 Lot number: N/A
 Physical description: Lyophilized powder
 Molecular weight: 3511.4
 Package and storage condition: stored at −80° C.
 Product identification: Anti-PD-1 antibody
 Manufacturer: WuXiAppTec
 Lot number: 3055W160405
 Physical description: Liquid
 Concentration: 11.5 mg/ml
 Package and storage condition: stored at −80° C.
Experimental Methods and Procedures
Cell Culture
 The 3LL tumor cells were maintained in vitro as a monolayer culture in medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase will be harvested and counted for tumor inoculation.
Tumor Inoculation
 Each mouse was inoculated subcutaneously at the right flank with 3LL tumor cells (1×106) in 0.1 ml of PBS for tumor development. The animals were randomized and treatment was started when the average tumor volume reaches approximately 105 mm³ for the efficacy study. The test article administration and the animal numbers in each group were shown in the experimental design table (Table 52).

TABLE 53

Testing Article Formulation Preparation

| Test article | Con. (mg/ml) | Formulation | Buffer |
|---|---|---|---|
| Vehicle1 | — | 25 mM Histidine pH 7, 10% Sucrose | — |
| Vehicle2 | — | 20 mM Histidine pH 5, 5% Sucrose | — |
| BT1718 | 1.0 | Add 10 mg BT1718 into 10 ml buffer, sonicate and shake to ensure the solution to be clear | 25 mM Histidine pH 7, 10% Sucrose |
|  | 0.3 | Add 900 ul 1.0 mg/ml BT1718 into 2.1 ml buffer, shake to ensure the solution to be clear |  |
|  | 0.1 | Add 300 ul 1.0 mg/ml BT1718 into 2.7 ml buffer, shake to ensure the solution to be clear |  |
| PD-1 | 1 | Add 348 ul 11.5 mg/ml PD-1 into 3.652 ml buffer, shake to ensure the solution to be clear | 20 mM Histidine pH 5, 5% Sucrose |

Observations
 All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.
Tumor Measurements and the Endpoints
 The major endpoint was to see if the tumor growth could be delayed or mice could be cured. Tumor size was measured three times weekly in two dimensions using a caliper, and the volume was expressed in mm³ using the formula: $V=0.5\ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.
 TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant.

Results

Figure 7:
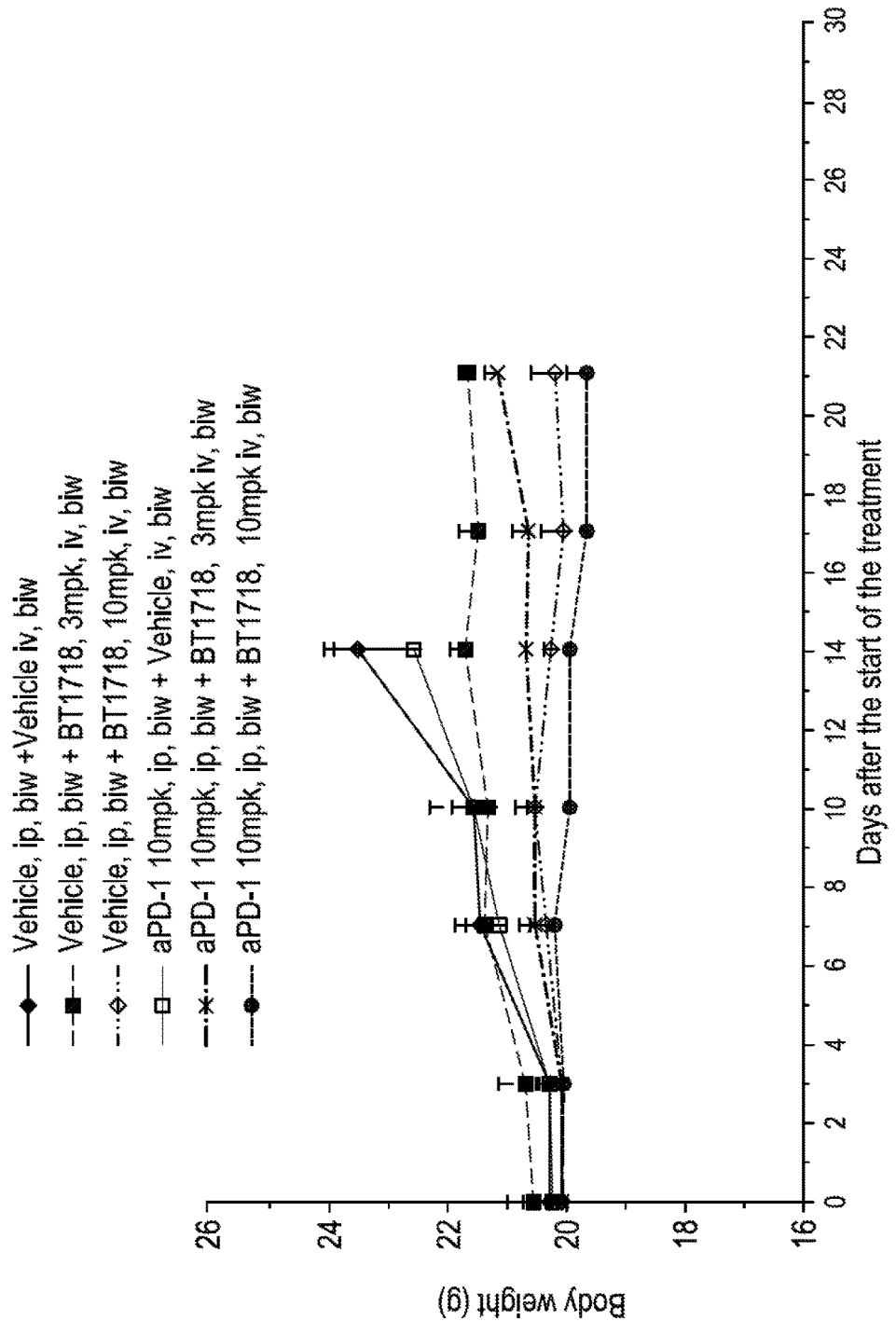
FIG. 7 depicts body weight changes after the treatment of BT1718 and PD-1 to C57BL/6 mice bearing 3LL tumor. Data points represent group mean body weight. Error bars represent standard error of the mean (SEM).

The body weight curve is depicted in FIG. 7.

FIG. 7 displays body weight changes after the treatment of BT1718 and PD-1 to C57BL/6 mice bearing 3LL tumor. Data points represent group mean body weight. Error bars represent standard error of the mean (SEM).

Tumor Volume Trace

Mean tumor volume over time in female C57BL/6 mice bearing 3LL is shown in Table 54.

TABLE 54

| | | Tumor volume trace over time | | | | | | |
|---|---|---|---|---|---|---|---|---|
| | | Days after the start of treatment | | | | | | |
| Gr. | Treatment | 0 | 3 | 7 | 10 | 14 | 17 | 21 |
| 1 | Vehicle, ip, biw + Vehicle, iv, biw | 96 ± 9 | 170 ± 14 | 474 ± 44 | 825 ± 105 | 2001 ± 289 | | |
| 2 | Vehicle, ip, biw + BT1718, 3 mpk, iv, biw | 96 ± 7 | 167 ± 29 | 320 ± 71 | 396 ± 79 | 612 ± 133 | 968 ± 211 | 1177 ± 196 |
| 3 | Vehicle, ip, biw + BT1718, 10 mpk, iv, biw | 96 ± 6 | 134 ± 17 | 141 ± 18 | 128 ± 16 | 132 ± 26 | 129 ± 33 | 104 ± 41 |
| 4 | PD-1, 10 mpk, ip, biw + Vehicle, iv, biw | 96 ± 6 | 175 ± 14 | 470 ± 87 | 672 ± 161 | 1549 ± 423 | | |
| 5 | PD-1, 10 mpk, ip, biw + BT1718, 3 mpk, iv, biw | 96 ± 9 | 148 ± 17 | 196 ± 31 | 237 ± 68 | 265 ± 78 | 311 ± 93 | 447 ± 136 |
| 6 | PD-1, 10 mpk, ip, biw + BT1718, 10 mpk, iv, biw | 96 ± 6 | 133 ± 13 | 133 ± 35 | 104 ± 29 | 69 ± 21 | 45 ± 17 | 36 ± 13 |

Tumor Growth Curve

Figure 8:
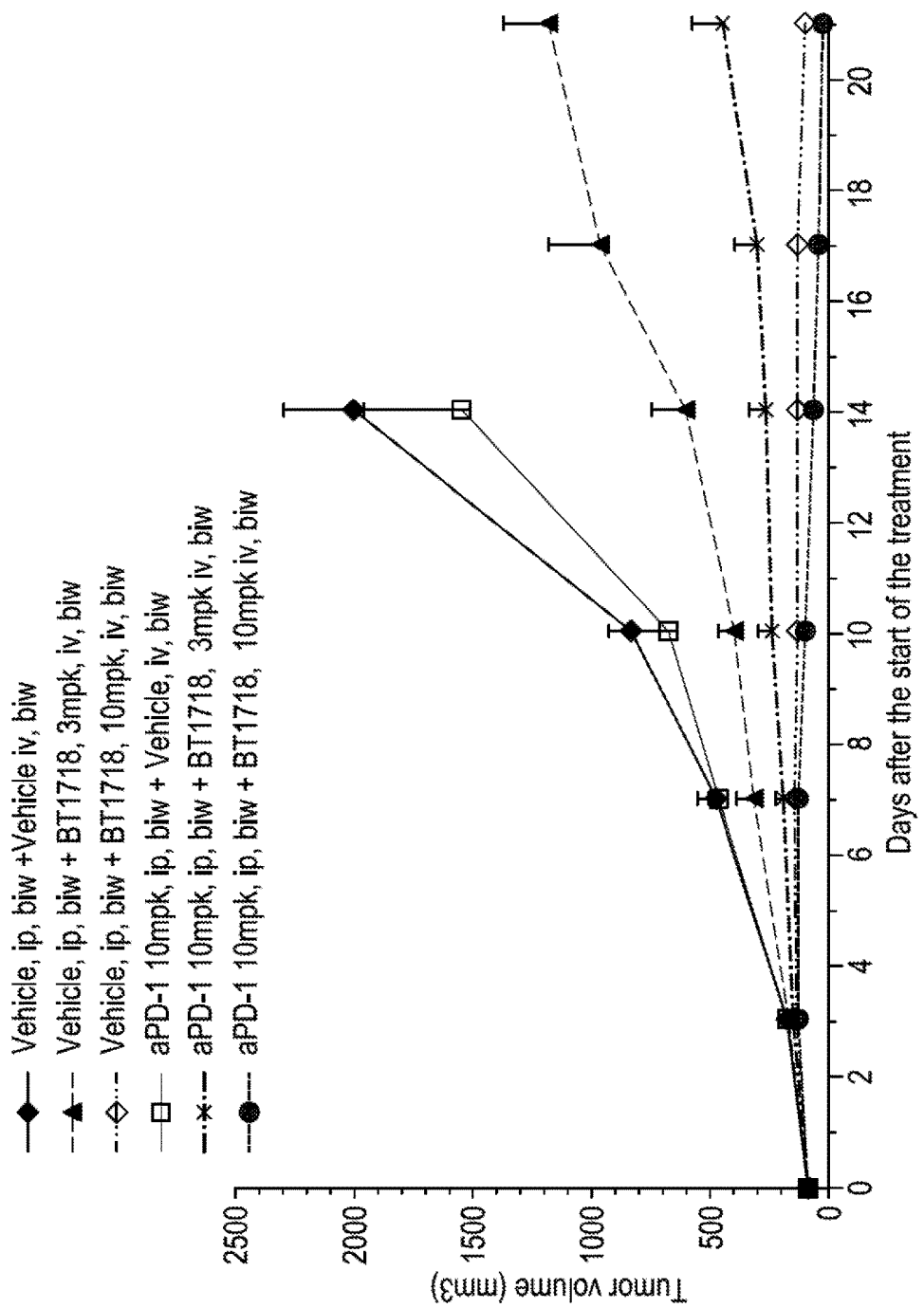
FIG. 8 depicts the tumor volume trace after administering BT1718 and PD-1 to the C57BL/6 mice bearing 3LL tumor. Data points represent group mean, error bars represent standard error of the mean (SEM).

The tumor growth curve is shown in FIG. 8.

FIG. 8 displays the tumor volume trace after administering BT1718 and PD-1 to the C57BL/6 mice bearing 3LL tumor. Data points represent group mean, error bars represent standard error of the mean (SEM).

Tumor Growth Inhibition Analysis

Tumor growth inhibition rate for BT1718 and Anti-PD-1 antibody in the 3LL syngeneic model was calculated based on tumor volume measurements at day 14 after the start of treatment.

TABLE 55

| | | Tumor growth inhibition analysis (T/C and TGI) | | | | |
|---|---|---|---|---|---|---|
| Gr | Treatment | Tumor Volume (mm³)[a] | T/C[b] (%) | TGI (%) | P value (vs Vehicle) | P value(vs single group) |
| 1 | Vehicle, ip, biw + Vehicle, iv, biw | 2001 ± 289 | — | — | — | |
| 2 | Vehicle, ip, biw + BT1718, 3 mpk, iv, biw | 612 ± 133 | 30.6 | 72.9 | p < 0.001 | |
| 3 | Vehicle, ip, biw + BT1718, 10 mpk, iv, biw | 132 ± 26 | 6.6 | 98.1 | p < 0.001 | |
| 4 | PD-1, 10 mpk, ip, biw + Vehicle, iv, biw | 1549 ± 423 | 77.4 | 23.7 | p > 0.05 | |
| 5 | PD-1, 10 mpk, ip, biw + BT1718, 3 mpk, iv, biw | 265 ± 78 | 13.2 | 91.2 | p < 0.001 | P < 0.05 |
| 6 | PD-1, 10 mpk, ip, biw + BT1718, 10 mpk, iv, biw | 69 ± 21 | 3.4 | 101.4 | p < 0.001 | P > 0.05 |

[a]Mean ± SEM.

[b]Tumor Growth Inhibition is calculated by dividing the group average tumor volume for the treated group by the group average tumor volume for the control group (T/C).

Summary and Discussion

In this study, the in vivo anti-tumor efficacy of BT1718 alone or in combination with Anti-PD-1 antibody in 3LL syngeneic model in C57BL/6 mice was evaluated. The measured body weights are shown in the FIG. 7. Tumor volume of all treatment groups at various time points are shown in Tables 54 and 55 and FIG. 7.

The mean tumor volume of vehicle treated mice reached 2001 mm$^3$ on day 14 after the start of treatment. 2/6 mice showed obvious response to anti-PD-1 antibody treatment while 4/6 mice didn't show any response. BT1718 at 3 mg/kg and 10 mg/kg produced dose-dependent anti-tumor effect with tumor measured at 612 mm$^3$ (TGI=72.9%, p<0.001) and 132 mm$^3$ (TGI=98.1%, p<0.001). Anti-PD-1 antibody in combination with BT1718 at 3 mg/kg and 10 mg/kg further improved the therapeutic effect of BT1718, and tumors were measured at 265 mm$^3$ (TGI=91.2%, p<0.001 vs vehicle; p<0.05 vs BT1718 3 mg/kg) and 69 mm$^3$ (TGI=101.4%, p<0.001 vs vehicle; p>0.05 vs BT1718 10 mg/kg) respectively.

In this study, all mice maintained their bodyweight well.

We claim:

1. A method of treating cancer in a patient, wherein the cancer is selected from the group consisting of a sarcoma, lung cancer, breast cancer, colon cancer, gastric cancer, and head and neck cancer, comprising administering to said patient a therapeutically effective amount of BT1718, or a pharmaceutically acceptable salt and/or composition thereof, wherein
- the sarcoma is an N-ras mutant/IDH1 mutant soft tissue sarcoma (STS);
- the lung cancer is a Met-amplified squamous NSCLC, a Squamous cell NSCLC with wt EGFR, or a T790M EGFR-expressing lung adenocarcinoma;
- the breast cancer is a triple negative breast cancer;
- the colon cancer is a colorectal adenocarcinoma;
- the gastric cancer is a FGFR-amplified gastric cancer; and
- the head and neck cancer is a nasal septum squamous cell carcinoma, and wherein BT1718 is a Bicycle drug conjugate of formula:

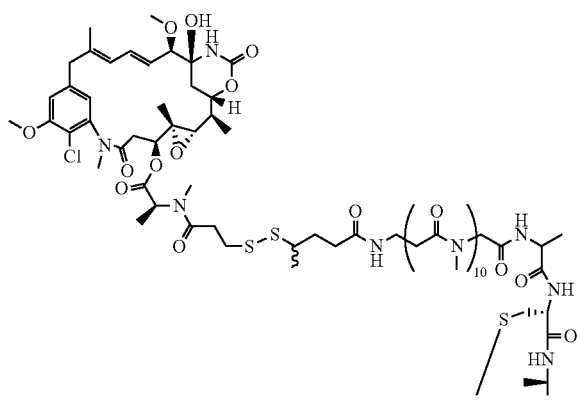
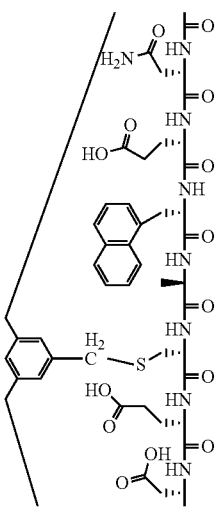
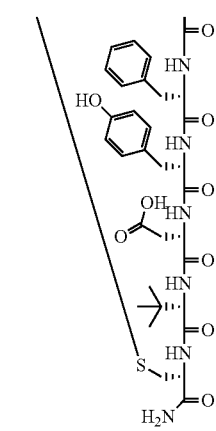

2. The method of claim 1, wherein the cancer is an N-ras mutant/IDH1 mutant soft tissue sarcoma (STS).

3. The method of claim 1, wherein the cancer is a triple negative breast cancer.

4. The method of claim 3, wherein the triple negative breast cancer is a basaloid triple negative breast cancer.

5. The method of claim 1, wherein the cancer is a colorectal adenocarcinoma.

6. The method of claim 1, wherein the cancer is a FGFR-amplified gastric cancer.

7. The method of claim 1, wherein the cancer is a nasal septum squamous cell carcinoma.

8. A method of treating cancer in a patient, wherein the cancer is selected from the group consisting of a sarcoma, lung cancer, breast cancer, colon cancer, gastric cancer, and head and neck cancer, comprising administering to said patient a minimally effective dose of BT1718, or a pharmaceutically acceptable salt and/or composition thereof, wherein the minimally effective dose leads to tumor-stasis when administered intravenous twice a week (IV BIW), wherein the sarcoma is an N-ras mutant/IDH1 mutant soft tissue sarcoma (STS);

the lung cancer is a Met-amplified squamous NSCLC, a Squamous cell NSCLC with wt EGFR, or a T790M EGFR-expressing lung adenocarcinoma;

the breast cancer is a triple negative breast cancer;

the colon cancer is a colorectal adenocarcinoma;

the gastric cancer is a FGFR-amplified gastric cancer; and the head and neck cancer is a nasal septum squamous cell carcinoma, and wherein BT1718 is a Bicycle drug conjugate of formula:

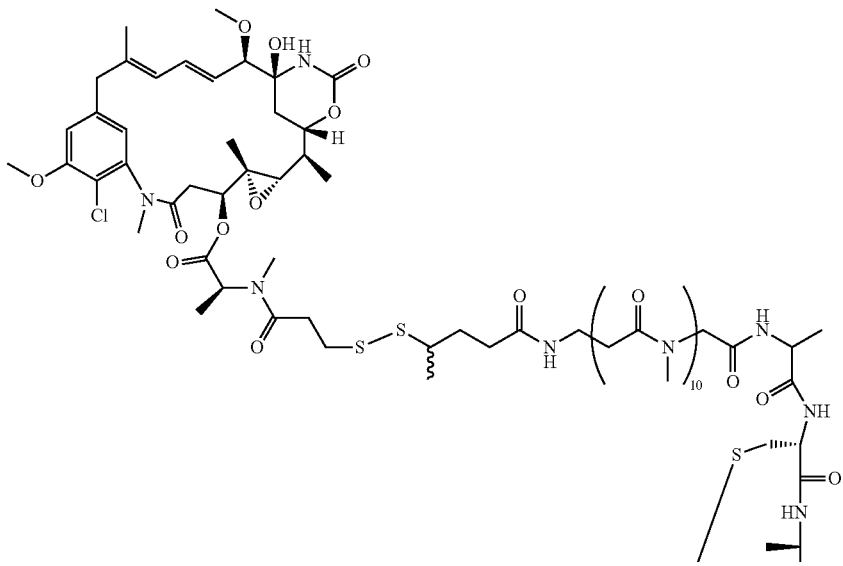

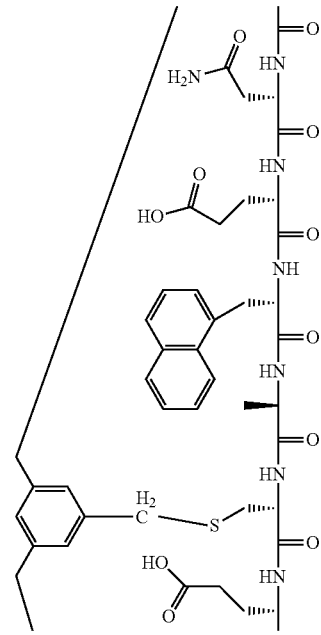

-continued

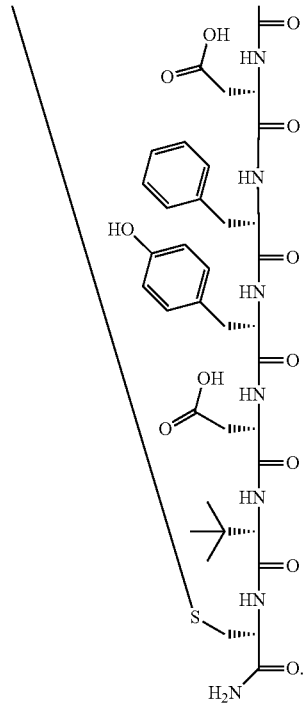

9. The method of claim 8, wherein the cancer is a triple negative breast cancer, and the minimally effective dose is <10 mg/kg.

10. The method of claim 8, wherein the cancer is a FGFR-amplified gastric cancer, and the minimally effective dose is 3 mg/kg.

11. The method of claim 8, wherein the cancer is an N-ras mutant/IDH1 mutant soft tissue sarcoma (STS), and the minimally effective dose is <3 mg/kg.

12. The method of claim 8, wherein the cancer is a basaloid triple negative breast cancer, and the minimally effective dose is <10 mg/kg.

13. The method of claim 8, wherein the cancer is a high pgp-expressing colorectal adenocarcinoma, and the minimally effective dose is >10 mg/kg.

14. The method of claim 8, wherein the cancer is a colorectal adenocarcinoma, and the minimally effective dose is 10 mg/kg.

15. The method of claim 8, wherein the cancer is a nasal septum squamous cell carcinoma, and the minimally effective dose is 10 mg/kg.

16. The method of claim 8, wherein the cancer is a Met-amplified squamous NSCLC, and the minimally effective dose is <10 mg/kg.

17. The method of claim 8, wherein the cancer is a Squamous cell NSCLC with wt EGFR, and the minimally effective dose is <10 mg/kg.

18. The method of claim 8, wherein the cancer is a T790M EGFR-expressing lung adenocarcinoma, and the minimally effective dose is <10 mg/kg.

19. The method of claim 5, wherein the colorectal adenocarcinoma is a high pgp-expressing colorectal adenocarcinoma.

20. The method of claim 1, wherein the cancer is a Met-amplified squamous NSCLC.

21. The method of claim 1, wherein the cancer is a Squamous cell NSCLC with wt EGFR.

22. The method of claim 1, wherein the cancer is a T790M EGFR-expressing lung adenocarcinoma.

* * * * *